United States Patent
Kikuchi et al.

(10) Patent No.: US 11,651,859 B2
(45) Date of Patent: May 16, 2023

(54) METHOD FOR PREDICTING SEVERITY AND PROGNOSIS OF CARDIOVASCULAR DISEASE

(71) Applicants: NATIONAL UNIVERSITY CORPORATION NAGOYA UNIVERSITY, Nagoya (JP); SYSMEX CORPORATION, Kobe (JP)

(72) Inventors: Ryosuke Kikuchi, Nagoya (JP); Kazuhiro Harada, Nagoya (JP); Yohei Shibata, Nagoya (JP); Hideki Ishii, Nagoya (JP); Toyoaki Murohara, Nagoya (JP)

(73) Assignees: NATIONAL UNIVERSITY CORPORATION NAGOYA UNIVERSITY, Nagoya (JP); SYSMEX CORPORATION, Kobe (JP)

( * ) Notice: Subject to any disclaimer, the term of this patent is extended or adjusted under 35 U.S.C. 154(b) by 1182 days.

(21) Appl. No.: 16/227,097

(22) Filed: Dec. 20, 2018

(65) Prior Publication Data

US 2019/0198170 A1    Jun. 27, 2019

(30) Foreign Application Priority Data

Dec. 25, 2017    (JP) .............................. JP2017-247153

(51) Int. Cl.
*G16H 50/30* (2018.01)
*G16H 50/20* (2018.01)
(Continued)

(52) U.S. Cl.
CPC ......... *G16H 50/20* (2018.01); *G01N 33/6827* (2013.01); *G01N 33/6863* (2013.01);
(Continued)

(58) Field of Classification Search
CPC ........ G16H 50/20; G16H 50/30; G16B 20/20; G01N 33/6827; G01N 33/6863;
(Continued)

(56) References Cited

U.S. PATENT DOCUMENTS 10,408,845 B2 *   9/2019   Snider ...................... A61P 9/00
11,254,738 B2 *   2/2022   Fellouse ................ A61P 35/00
(Continued)

FOREIGN PATENT DOCUMENTS

| JP | 2014-505259 A | 2/2014 |
| JP | 2014-520523 A | 8/2014 |

(Continued)

OTHER PUBLICATIONS

Joshua M Boucher & Victoria L Bautch; "Antiangiogenic VEGF-A in peripheral artery disease;" Dec. 2014; Nature Medicine; vol. 20, No. 12; pp. 1383-1384. (Year: 2014).*

(Continued)

*Primary Examiner* — John E Breene
*Assistant Examiner* — Christine Y Liao
(74) *Attorney, Agent, or Firm* — Sughrue Mion, PLLC

(57) ABSTRACT

Disclosed is a method comprising acquiring a value relating to VEGF-A of a subject, wherein the value is a measured value of total VEGF-A in a blood sample, or a value obtained by dividing a measured value of VEGF-$A_{165}$b in the blood sample by a measured value of total VEGF-A in the blood sample (VEGF-$A_{165}$b/total VEGF-A), and the value suggests prognosis of myocardial infarction of the subject or severity of coronary artery disease of the subject.

10 Claims, 11 Drawing Sheets

(51) Int. Cl.
G01N 33/68 (2006.01)
G01N 33/96 (2006.01)
G16B 20/20 (2019.01)

(52) U.S. Cl.
CPC ......... *G01N 33/6893* (2013.01); *G01N 33/96* (2013.01); *G16B 20/20* (2019.02); *G16H 50/30* (2018.01); *G01N 2800/324* (2013.01); *G01N 2800/325* (2013.01)

(58) Field of Classification Search
CPC ............... G01N 33/6893; G01N 33/96; G01N 2800/324; G01N 2800/325
See application file for complete search history.

(56) References Cited

U.S. PATENT DOCUMENTS

| | | | | |
|---|---|---|---|---|
| 2010/0255520 | A1* | 10/2010 | Kavsak | G01N 33/6869 435/20 |
| 2013/0337476 | A1* | 12/2013 | Lee | G01N 33/6893 435/7.92 |
| 2015/0126860 | A1* | 5/2015 | Beymer | A61B 6/504 600/431 |

FOREIGN PATENT DOCUMENTS

| | | |
|---|---|---|
| WO | 2009079773 A1 | 7/2009 |
| WO | 2012/106152 A1 | 8/2012 |
| WO | 2013/005053 A2 | 1/2013 |

OTHER PUBLICATIONS

Luisa Hueso, et al., "Dynamics and implications of circulating anti-angiogenic VEGF-A165b isoform in patients with ST-elevation myocardial infarction", Scientific Reports, 2017, pp. 1-14, vol. 7, 9962.

Kyoko Matsudaira, MD, et al., "Impact of Low Levels of Vascular Endothelial Growth Factor After Myocardial Infarction on 6-Month Clinical Outcome", Circulation Journal, Jun. 2012; pp. 1509-1516; vol. 76.

Christopher Heeschen, MD, et al., "Prognostic Significance of Angiogenic Growth Factor Serum Levels in Patients With Acute Coronary Syndromes", Circulation, 2003, pp. 524-530, vol. 107.

Anwar Jewel Siddiqui et al., "Depressed expression of angiogenic growth factors in the subacute phase of myocardial ischemia: a mechanism behind the remodeling plateau?" Coronary Artery Disease, 2010, vol. 21, No. 2, pp. 65-71 (7 pages total).

Communication, dated Feb. 26, 2019, issued by the European Patent Office in counterpart European Patent Application No. 18215249.6.

Communication, dated Mar. 17, 2020, issued by the European Patent Office in European Patent Application No. 18 215 249.6.

Notice of Reasons for Refusal, dated Sep. 14, 2021, issued by the Japanese Patent Office in Japanese Patent Application No. 2017-247153.

* cited by examiner

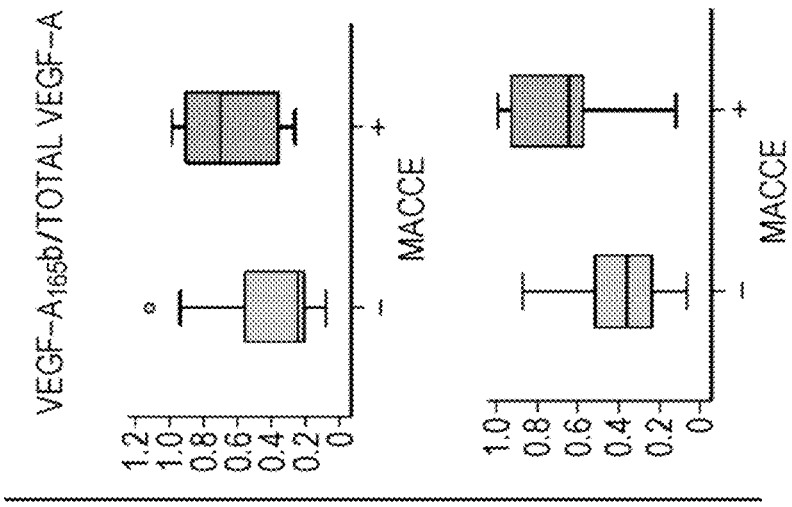
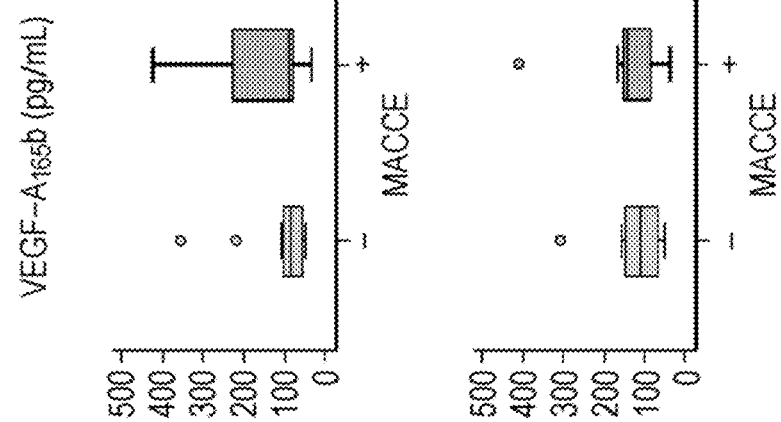
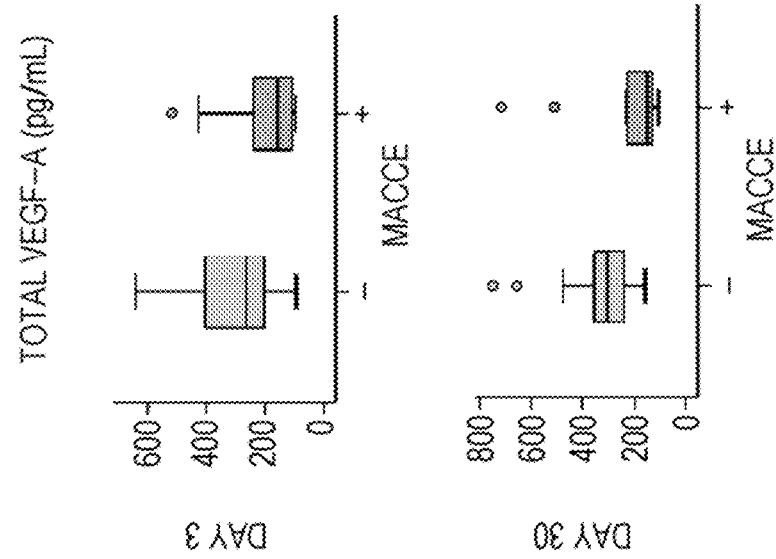

METHOD FOR PREDICTING SEVERITY AND PROGNOSIS OF CARDIOVASCULAR DISEASE

CROSS REFERENCE TO RELATED APPLICATIONS

This application claims priority from prior Japanese Patent Application No. 2017-247153, filed on Dec. 25, 2017, entitled "METHOD, APPARATUS AND COMPUTER PROGRAM FOR PREDICTING SEVERITY AND PROGNOSIS OF CARDIOVASCULAR DISEASE USING MEASURED VALUE RELATING TO VEGF-A IN BLOOD OF SUBJECT", the entire contents of which are incorporated herein by reference.

TECHNICAL FIELD

A method, an apparatus and a computer program for acquiring a value relating to VEGF-A of a subject are disclosed.

BACKGROUND

Cardiovascular disease is a generic term for diseases caused by cardiac insufficiency, and it is a severe disease group which is one of the main causes of death.

In Scientific Reports 7, Article number: 9962 (2017) doi: 10.1038/s41598-017-10505-9, VEGF-$A_{165}$b has been measured in patients with ST elevation type acute myocardial infarction, the size of myocardial infarction has been examined by nuclear magnetic resonance imaging (MRI), and it has been shown that patients with elevated VEGF-$A_{165}$b at 24 hours after onset have a broad infarction range and decreased left ventricular ejection fraction.

Myocardial infarction is one of cardiovascular diseases with a poor prognosis, although the mortality rate tends to decrease due to improved treatment.

Stenosis and obstruction of a vessel lumen in a coronary artery that nourishes the heart is one of the major causes of myocardial infarction. A SYNTAX (SYNergy between PCI with TAXUS™ and Cardiac Surgery) score is known as an index for calculating the complexity of coronary artery disease from the anatomical features of lesions in coronary arteries. Since the SYNTAX score is scored using angiograms, it is necessary to administer an angiographic agent and perform angiography on each patient. For this reason, evaluation of the severity of coronary artery disease based on the SYNTAX score is very complicated and invasiveness to the patient is also high.

SUMMARY

The scope of the present invention is defined solely by the appended claims, and is not affected to any degree by the statements within this summary.

A present invention relates to a method including acquiring a value relating to VEGF-A of a subject. The value includes a measured value of total VEGF-A in a blood sample, or a value obtained by dividing a measured value of VEGF-$A_{165}$b in the blood sample by a measured value of total VEGF-A in the blood sample (VEGF-$A_{165}$b/total VEGF-A).

BRIEF DESCRIPTION OF THE DRAWINGS

FIG. 10A shows box plots of measured values of total VEGF-A on Day 3 and Day 30 after onset of myocardial infarction.
FIG. 10B shows box plots of measured values of VEGF-$A_{165}$b on Day 3 and Day 30 after the onset of myocardial infarction.
FIG. 10C shows box plots of VEGF-$A_{165}$b/total VEGF-A on Day 3 and Day 30 after the onset of myocardial infarction. + shows a group in which MACCE was observed and − shows a group in which MACCE was not observed.

DETAILED DESCRIPTION OF THE PREFERRED EMBODIMENTS

[1. Method]

Figure 1:
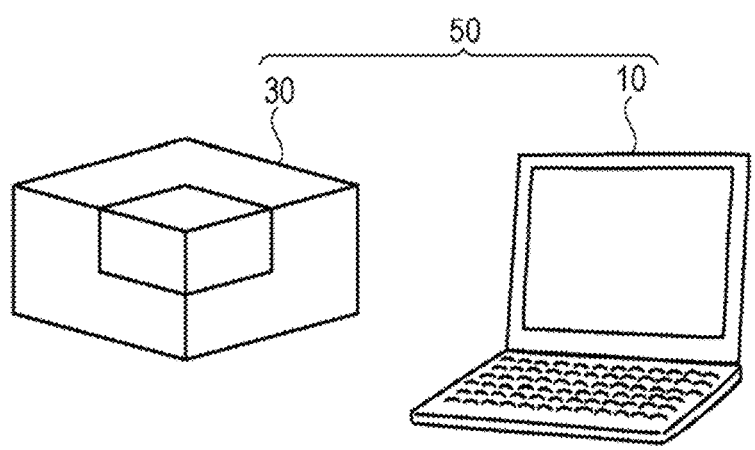
FIG. 1 is a view showing an outline of an apparatus.

The method includes acquiring a value relating to VEGF-A of a subject. The value relating to VEGF-A includes a measured value of total VEGF-A in a blood sample, and/or a value obtained by dividing a measured value of VEGF-$A_{165}$b in the blood sample by a measured value of total VEGF-A in the blood sample (VEGF-$A_{165}$b/total VEGF-A). The method may include a step of acquiring a measured value of total VEGF-A in the blood sample of the subject, and/or a measured value of VEGF-$A_{165}$b (hereinafter also referred to as "measured value relating to VEGF-A"). The acquisition of the measured value of total VEGF-A and VEGF-$A_{165}$b/total VEGF-A may be simultaneous or may have a time difference. The acquisition of the measured value of total VEGF-A and the measured value of VEGF-$A_{165}$b may be simultaneous or may have a time difference. In the method, the value suggests prognosis of myocardial infarction of the subject or severity of coronary artery disease of the subject. Preferably, the above suggestion includes predicting the prognosis of myocardial infarction of the subject or the severity of coronary artery disease of the subject, assisting the prognosis of myocardial infarction of the subject or the severity of coronary artery disease of the subject, or determining the prognosis of myocardial infarction of the subject or the severity of coronary artery disease of the subject.

The method may include obtaining a comparison result between each value relating to VEGF-A and a corresponding reference value. The suggestion may be made based on the comparison result.

The above method may be carried out by humans, or may be realized by an apparatus 10 to be described later.

[1-1. Method for Acquiring Measured Value Relating to VEGF-A]

The subject is not particularly limited as long as it is an individual who needs suggestions on the prognosis of myocardial infarction or the severity of coronary artery disease by the above method. The individual includes humans and non-human mammals. Examples of the mammal include bovine, horse, sheep, goat, pig, dog, cat, rabbit, monkey, and the like. The individual is preferably human. The age and gender of the individual do not matter. The individual is preferably a living individual. The subject may be an individual not suspected of ischemic cardiovascular disease or coronary artery disease but is preferably an individual suspected of ischemic cardiovascular disease or coronary artery disease or an individual who developed ischemic cardiovascular disease or coronary artery disease. It is preferable that the subject in which the prognosis of myocardial infarction is suggested is an individual after onset of myocardial infarction. Suspected of coronary artery disease refers to a case where there is at least one subjective symptom selected from chest symptoms (chest pain, chest compression feeling, or the like), back pain, upper abdominal pain, shoulder pain, breathlessness, cold sweats and the like, a case where an abnormality is found in electrocardiogram or subjective symptom in exercise tolerance test, and/or a case where an abnormality is found by myocardial scintigraphy, or the like.

The ischemic disease is not limited as long as it is a lesion occurring in myocardial tissue accompanying circulatory disorder. Examples of the ischemic disease include angina pectoris and myocardial infarction. Preferably, it is myocardial infarction. The definition of myocardial infarction follows the third universal definition of myocardial infarction (Circulation 2012; 126: 2020-2035). The prognosis of myocardial infarction can be evaluated by, for example, whether or not major adverse cardiac and cerebrovascular events (MACCE) occur. Examples of the major adverse cardiac and cerebrovascular events include total death from onset to a remote period of myocardial infarction, recurrence of myocardial infarction, cerebrovascular accident, reapplication of revascularization of coronary artery and the like. Preferably, the major adverse cardiac and cerebrovascular events include one or more events selected from the group consisting of cardiovascular death, recurrence of nonfatal myocardial infarction, reapplication of coronary artery revascularization surgery, and cerebral infarction.

The coronary artery disease is not limited as long as it is a lesion occurring in a coronary artery blood vessel that nourishes the heart. Preferably, the coronary artery disease is accompanied by stenosis and/or obstruction of the vessel lumen. The definition of coronary artery disease and the evaluation of complexity are in accordance with Sianos, et al. (Journal of EuroPCR in collaboration with the Working Group on Interventional Cardiology of the European Society of Cardiology 2005; 1: 219-227). For example, according to Sianos, et al., the severity of coronary artery disease can be evaluated by SYNTAX (SYNergy between PCI with TAXUS™ and Cardiac Surgery) score obtained by scoring the complexity of coronary artery disease by angiograms. For example, when the SYNTAX score of a subject is more than 22, the coronary artery disease of the subject can be evaluated as severe. When the SYNTAX score of the subject is 22 or less, the coronary artery disease of the subject can be evaluated as not severe (non-severe). Preferably, when the SYNTAX score of the subject is 22 or less and more than 0, the coronary artery disease of the subject can be evaluated as not severe (non-severe). When the SYNTAX score of the subject is more than 33, the coronary artery disease of the subject may be evaluated as high in severity. When the SYNTAX score of the subject is 33 or less and more than 22, the coronary artery disease of the subject may be evaluated as moderate in severity. Coronary artery disease is determined as significant stenosis when 75% or more (50% or more in the main trunk of the left coronary artery) stenosis and/or obstruction in the coronary artery lumen is observed in an angiographic examination. Therefore, individuals without significant stenosis may be used as a negative control group for coronary artery disease. The negative control group may be defined as a group with a SYNTAX score of 0.

From the subject, individuals who are predicted that the measured value of total VEGF-A and/or the measured value of VEGF-$A_{165}$b are changed due to causes other than ischemic diseases of the heart and/or the brain and coronary artery disease are excluded. Preferably, individuals who are undergoing (or have received) hemodialysis, individuals with malignancies requiring surgical treatment or chemotherapy in the previous year, individuals with malignancies, and individuals with an autoimmune disease such as collagen disease and the like are excluded.

The total VEGF-A and VEGF-$A_{165}$b present in the blood (preferably in the circulating blood) are to be measured, and preferably, those present in the plasma or serum are to be measured. Whole blood collected from an individual, and plasma or serum separated from whole blood collected from an individual are called a blood sample. As an anticoagulant used for collecting the plasma, it is preferable to use other than heparin or a salt thereof. In the case of collecting a blood sample at catheter examination, it is preferably performed before administering heparin to an individual. The type of the blood sample of the subject used for measurement and the type of the blood sample used for determining a predetermined reference value may be the same as or different from each other, but are preferably the same as each other. When plasma is used as the blood sample, it is preferable that the plasma for determining the predetermined reference value is prepared from blood collected using the same anticoagulant as in the plasma of the subject. The blood sample may be a fresh sample or may be a preserved sample. When preserving the blood sample, it can be preserved in a room temperature environment, a refrigerated environment, or a frozen environment, but frozen preservation is preferable. The blood sample is preferably serum.

VEGF-A intends vascular endothelial growth factor A, and in humans, for example, a product derived from a gene registered in Gene ID: 7422 in National Center for Biotechnology Information is intended. The total VEGF-A is intended to include all variants translated from a VEGF-A gene via transcription. VEGF-$A_{165}$b is one of variants transcribed and translated from a VEGF-A gene, and is, for example, reported in Cancer research 2002: 62: 4123-4131. VEGF-$A_{165}$b is also referred to as VEGF$_{165}$b.

The "measured value" refers to a value reflecting the amount or concentration of total VEGF-A or VEGF-$A_{165}$b protein (hereinafter referred to as target protein). When the measured value is indicated by "amount", it may be expressed on either a mole basis or a mass basis, but it is preferable to indicate the amount on a mass basis. When the value is expressed in terms of "concentration", it may be a molar concentration or a ratio of a mass (mass/volume) per constant volume of a blood sample, but the value is preferably expressed in terms of a ratio of mass/volume. In addition to the above, the value reflecting the amount or the concentration may be the intensity of a signal such as fluorescence or luminescence.

The "corresponding reference value" refers to a reference value determined according to each value relating to VEGF-A. It is preferable that the reference value is predetermined. The reference value used for suggesting the prognosis of myocardial infarction is preferably determined from the value relating to VEGF-A in blood samples collected from a group of subjects after onset of myocardial infarction with a good prognosis. More preferably, the reference value is determined from the value relating to VEGF-A in the blood samples collected from a group of subjects after the onset of myocardial infarction with a good prognosis and the value relating to VEGF-A in blood samples collected from a group of subjects after the onset of myocardial infarction with a poor prognosis. The reference value used for suggesting the severity of coronary artery disease is preferably determined from the value relating to VEGF-A in blood samples collected from a severe coronary artery disease group. More preferably, the reference value is determined from the value relating to VEGF-A in blood samples collected from a non-severe coronary artery disease group and the value relating to VEGF-A in the blood samples collected from the severe coronary artery disease group.

For example, a value (positive control value) relating to VEGF-A collected from a group of one or more subjects after the onset of myocardial infarction with a poor prognosis and a value (negative control value) relating to VEGF-A in blood samples collected from a group of one or more subjects after the onset of myocardial infarction with a good prognosis are acquired. Alternatively, a value (positive control value) relating to VEGF-A collected from the severe coronary artery disease group and a value (negative control value) relating to VEGF-A collected from the non-severe coronary artery disease group are acquired. Based on these multiple values, a value that can most accurately classify the positive control value and the corresponding negative control value can be defined as a "reference value". The "value that can most accurately classify" can be appropriately set based on indicators such as sensitivity, specificity, positive predictive value, negative predictive value and the like depending on the purpose of the examination. The reference value can be also determined by a ROC curve (Receiver Operating Characteristic curve), a discriminant analysis method, a mode method, a Kittler method, a 3σ method, a p-tile method, and the like.

The method of acquiring the measured value relating to VEGF-A is not limited. For example, in order to acquire a measured value of target protein, an antibody capable of specifically binding to the target protein, that is, an anti-target protein antibody can be used. Examples of the method of acquiring a measured value of target protein using an anti-target protein antibody include an enzyme-linked immunosorbent assay (ELISA) method and a western blotting method.

Acquisition of the measured value of target protein using an anti-target protein antibody will be explained by taking the ELISA method as an example.

First, an anti-target protein antibody for capturing a target protein (hereinafter, "capture antibody") is mixed with a blood sample. The order of mixing the blood sample and the capture antibody is not particularly limited, and these may be mixed substantially simultaneously or sequentially mixed.

Specifically, a complex of the capture antibody and a target protein in the blood sample is first formed and then the complex is immobilized on a solid phase, or the capture antibody is immobilized on a solid phase in advance, and a complex of the immobilized capture antibody and a target protein in the blood sample can be formed. More preferred is an embodiment in which the complex is first formed and then the complex is immobilized on a solid phase. Then, the complex formed on a solid phase or a complex formed on a solid phase is detected by a method known in the art, whereby the measured value of target protein contained in the blood sample can be acquired.

In the case where a complex of the capture antibody and a target protein in the blood sample is first formed and then the complex is immobilized on a solid phase, the capture antibody modified with biotin or the like is brought into contact with the target protein in the blood sample to form a complex. By separately binding avidin or streptavidin (hereinafter also referred to as "avidins") to the solid phase in advance, the complex can be immobilized on the solid phase via binding between biotin and avidins.

In the case of immobilizing the capture antibody to the solid phase in advance, the mode of immobilization of the capture antibody to the solid phase is not particularly limited. For example, the capture antibody may be directly bound to the solid phase, or the capture antibody and the solid phase may be indirectly bound via another substance. Examples of the direct binding include physical adsorption and the like. Examples of the indirect binding include a bond via a combination with avidins. In this case, by modifying the capture antibody with biotin in advance and binding avidins to the solid phase in advance, the capture antibody and the solid phase can be indirectly bound via the binding between the biotin and the avidins. In this embodiment, it is preferable that the binding between the capture antibody and the solid phase is an indirect binding via biotin and avidins.

The material of the solid phase is not particularly limited, and it can be selected from, for example, organic polymer compounds, inorganic compounds, biopolymers, and the like. Examples of the organic polymer compound include latex, polystyrene, polypropylene, and the like. Examples of the inorganic compound include magnetic bodies (iron oxide, chromium oxide, ferrite, etc.), silica, alumina, glass, and the like. Examples of the biopolymer include insoluble agarose, insoluble dextran, gelatin, cellulose, and the like. Two or more of these may be used in combination. The shape of the solid phase is not particularly limited, and examples thereof include particles, membranes, microplates, microtubes, test tubes, and the like. Among them, particles are preferable, and magnetic particles are particularly preferable.

Bound/Free (B/F) separation for removing unreacted free components not forming a complex may be carried out after formation of the complex, preferably after formation of the complex and before detection of a labeling substance. The unreacted free component refers to a component not constituting a complex. Examples of the unreacted free component include an anti-target protein antibody not bound to the target protein, and the like. The means of B/F separation is not particularly limited, and when the solid phase is a particle, B/F separation can be performed by recovering only the solid phase capturing the complex by centrifugation. When the solid phase is a container such as a microplate or a microtube, B/F separation can be performed by removing a liquid containing an unreacted free component. When the solid phase is a magnetic particle, B/F separation can be performed by aspirating and removing a liquid containing an unreacted free component by a nozzle while magnetically constraining the magnetic particles with a magnet. This method is preferable from the viewpoint of automation. After removing the unreacted free component, the solid phase capturing the complex may be washed with a suitable aqueous medium such as phosphate buffered saline (PBS).

The complex can be detected, for example, using an anti-target protein antibody labeled with a labeling substance, or using an unlabeled anti-target protein antibody and an anti-immunoglobulin antibody labeled with a labeling substance capable of binding to the unlabeled anti-target protein antibody or the like, but it is preferable to use a labeled anti-target protein antibody. An epitope in the target protein of the labeled anti-target protein antibody is preferably different from an epitope in the target protein of the anti-target protein antibody that binds to the solid phase.

The labeling substance used for the labeled anti-target protein antibody or the labeled anti-immunoglobulin antibody is not particularly limited as long as the labeling substance generates a detectable signal. For example, it may be a substance which itself generates a signal (hereinafter also referred to as "signal generating substance") or a substance which catalyzes the reaction of other substances to generate a signal. Examples of the signal generating substance include fluorescent substances, radioactive isotopes, and the like. Examples of the substance that catalyzes the reaction of other substances to generate a detectable signal include enzymes. Examples of the enzymes include alkaline phosphatase (ALP), peroxidase, β-galactosidase, luciferase, and the like. Examples of the fluorescent substance include fluorescent dyes such as fluorescein isothiocyanate (FITC), rhodamine and Alexa Fluor (registered trademark), fluorescent proteins such as Enhanced green fluorescent protein (EGFP), and the like. Examples of the radioactive isotopes include $^{125}I$, $^{14}C$, $^{32}P$, and the like. Among them, an enzyme is preferable, and ALP is particularly preferable as a labeling substance.

The labeled anti-target protein antibody is obtained by labeling the anti-target protein antibody with the above-mentioned labeling substance by a labeling method known in the field of immunoassay technology. Labeling may also be performed using a commercially available labeling kit or the like. As the labeled immunoglobulin antibody, the same method as the labeling of the anti-target protein antibody may be used, or a commercially available product may be used.

By detecting a signal generated by the labeling substance of the labeled anti-target protein antibody contained in the complex, the measured value of the target protein contained in the blood sample can be acquired. The phrase "detecting a signal" herein includes qualitatively detecting the presence or absence of a signal, quantifying a signal intensity, and semi-quantitatively detecting the intensity of a signal. Semi-quantitative detection means to show the intensity of the signal in stages such as "no signal generated", "weak", "medium", "strong", and the like.

Methods for detecting a signal themselves are known in the field of immunoassay technology. In this embodiment, a measurement method according to the type of signal derived from the labeling substance may be appropriately selected.

For example, when the labeling substance is an enzyme, signals such as light and color generated by reacting a substrate for the enzyme can be measured by using a known apparatus such as a luminometer or a spectrophotometer.

The substrate of the enzyme can be appropriately selected from known substrates according to the type of the enzyme. For example, when ALP is used as the enzyme, examples of the substrate include chemiluminescent substrates such as CDP-Star (registered trademark) (disodium 4-chloro-3-(methoxyspiro[1,2-dioxetane-3,2'-(5'-chloro)tricyclo [3.3.1.1$^{3,7}$]decan]-4-yl)phenyl phosphate) and CSPD (registered trademark) (disodium 3-(4-methoxyspiro[1,2-dioxetane-3,2-(5'-chloro)tricyclo[3.1.1.3,7]decan]-4-yl) phenyl phosphate), and chromogenic substrates such as 5-bromo-4-chloro-3-indolyl phosphate (BCIP), disodium 5-bromo-6-chloro-indolyl phosphate and p-nitrophenyl phosphate. Particularly preferred is CDP-Star (registered trademark). The luminescence of the substrate is preferably detected with a luminometer.

When the labeling substance is a radioactive isotope, radiation as a signal can be measured using a known apparatus such as a scintillation counter. When the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

The detection result of the signal can be used as the measured value of target protein. For example, when quantitatively detecting the intensity of a signal, the measured value itself of the signal intensity or the value calculated from the measured value of the signal intensity can be used as the measured value of target protein. Examples of the value calculated from the measured value of the signal intensity include a value obtained by subtracting the measured value of the signal intensity of the negative control sample from the measured value of the signal intensity, a value obtained by dividing the measured value of the signal intensity by the measured value of the signal intensity of the positive control sample, combinations thereof, and the like. Examples of the negative control sample include blood samples of healthy individuals and the like. Examples of the positive control sample include blood samples containing target protein at a predetermined concentration.

The measured value of target protein in the blood sample can be calculated by creating a calibration curve from a measured value of the signal intensity of a positive control containing a known concentration of target protein and applying the measured value of the intensity of the signal derived from the target protein in the blood sample to the calibration curve. The measured value of target protein in the blood sample can be calculated by obtaining a regression equation from a measured value of the signal intensity of a positive control containing a known concentration of target protein without creating a calibration curve, and applying the measured value of the intensity of the signal derived from the target protein in the blood sample to the regression equation.

The anti-target protein antibody is not limited as long as it specifically binds to the target protein, and a polyclonal antibody, a monoclonal antibody, and a fragment thereof (for example, Fab, F(ab)2, or the like) obtained by immunizing nonhuman animals using a target protein or a part thereof as an antigen can be used. Also, immunoglobulin classes and subclasses are not particularly limited.

The target protein serving as an antigen used for preparing the anti-target protein antibody is not limited as long as an antibody of the target protein can be prepared. The target protein used as an antigen may be one extracted from mammalian cells by a known method or may be a recombinant protein obtained by recombinant genetic engineering technology. When a part of the target protein is used as an antigen, a fragment obtained by digesting the target protein with an enzyme or the like may be used, or a peptide having the same sequence as the amino acid sequence of a part of target protein may be used as an antigen. The peptide can be synthesized by a known method. Since it is preferable that the anti-target protein antibody used for acquiring the measured value of total VEGF-A reacts with all variants of VEGF-A, it is preferable that the anti-target protein antibody is prepared using an antigen having a peptide sequence common to all variants of VEGF-A. On the other hand, it is preferable that the anti-target protein antibody used for acquiring the measured value of VEGF-$A_{165}$b, particularly, the capture antibody, is prepared using an antigen having a peptide sequence specific to VEGF-$A_{165}$b. A commercially available product may be purchased for the anti-target protein antibody.

The measured value of target protein can also be acquired using a commercially available kit such as human VEGF Quantikine ELISA kit (DVE00, R&D), human vascular endothelial growth factor-$_{165}$b ELISA kit (MBS720132, MyBiosource), or the like.

[1-2. Suggestion on Prognosis of Myocardial Infarction]

The value relating to VEGF-A in the blood sample acquired by the method described in 1-1. above is used for suggesting the prognosis of myocardial infarction.

In a case where the subject is a subject after onset of myocardial infarction and the value relating to VEGF-A is a total VEGF-A measured value, in the comparison between the value relating to VEGF-A and a corresponding reference value, it is suggested that the prognosis of myocardial infarction of the subject is poor when the result that the total VEGF-A measured value is lower than the corresponding reference value is obtained. It may be suggested that the prognosis of myocardial infarction of the subject is good when the result that the total VEGF-A measured value is higher than the corresponding reference value is obtained.

In a case where the subject is a subject after the onset of myocardial infarction and the value relating to VEGF-A is VEGF-$A_{165}$b/total VEGF-A, in the comparison between the value relating to VEGF-A and a corresponding reference value, it is suggested that the prognosis of myocardial infarction of the subject is poor when the result that the VEGF-$A_{165}$b/total VEGF-A is higher than the corresponding reference value is obtained. It may be suggested that the prognosis of myocardial infarction of the subject is good when the result that the VEGF-$A_{165}$b/total VEGF-A is lower than the corresponding reference value is obtained.

In a case where the subject is a subject after the onset of myocardial infarction, with the date of onset as Day 1, the blood sample is collected from the subject on Day 1 to Day 40, preferably on Day 3 to Day 30, and more preferably on Day 3 and/or on Day 30.

In this section, for the terms common to the terms described in 1-1. above, the description of 1-1. above is incorporated herein.

[1-3. Suggestion on Severity of Coronary Artery Disease]

The value relating to VEGF-A in the blood sample acquired by the method described in 1-1. above is used for suggesting the severity of coronary artery disease.

In a case where the value relating to VEGF-A is a total VEGF-A measured value, in the comparison between the value relating to VEGF-A and a corresponding reference value, it is suggested that the subject belongs to a severe coronary artery disease group when the result that the total VEGF-A measured value is higher than the corresponding reference value is obtained. It may be suggested that the subject belongs to a non-severe coronary artery disease group when the result that the total VEGF-A measured value is lower than the corresponding reference value is obtained.

In a case where the value relating to VEGF-A is VEGF-$A_{165}$b/total VEGF-A, in the comparison between the value relating to VEGF-A and a corresponding reference value, it is suggested that the subject belongs to the severe coronary artery disease group when the result that the VEGF-$A_{165}$b/total VEGF-A is lower than the corresponding reference value is obtained. It may be suggested that the subject belongs to the non-severe coronary artery disease group when the VEGF-$A_{165}$b/total VEGF-A is higher than the corresponding reference value.

In this section, for the terms common to the terms described in 1-1. above, the description of 1-1. above is incorporated herein.

[2. Apparatus for Acquiring Measured Value on VEGF-A of Subject]

[2-1. Configuration of Apparatus]

An apparatus 10 for acquiring a measured value relating to VEGF-A of a subject includes at least a processing unit 101 and a storage unit. The storage unit is configured by a main storage unit 102 and/or an auxiliary storage unit 104. The apparatus 10 may be an apparatus for realizing the methods as defined in claims 1 to 13. In the description of the apparatus 10 and operations of the apparatus 10, for the terms common to the terms described in 1-1. above, the description of 1-1. above is incorporated herein.

The processing unit 101 acquires a value relating to VEGF-A in the blood sample of the subject.

Figure 2:
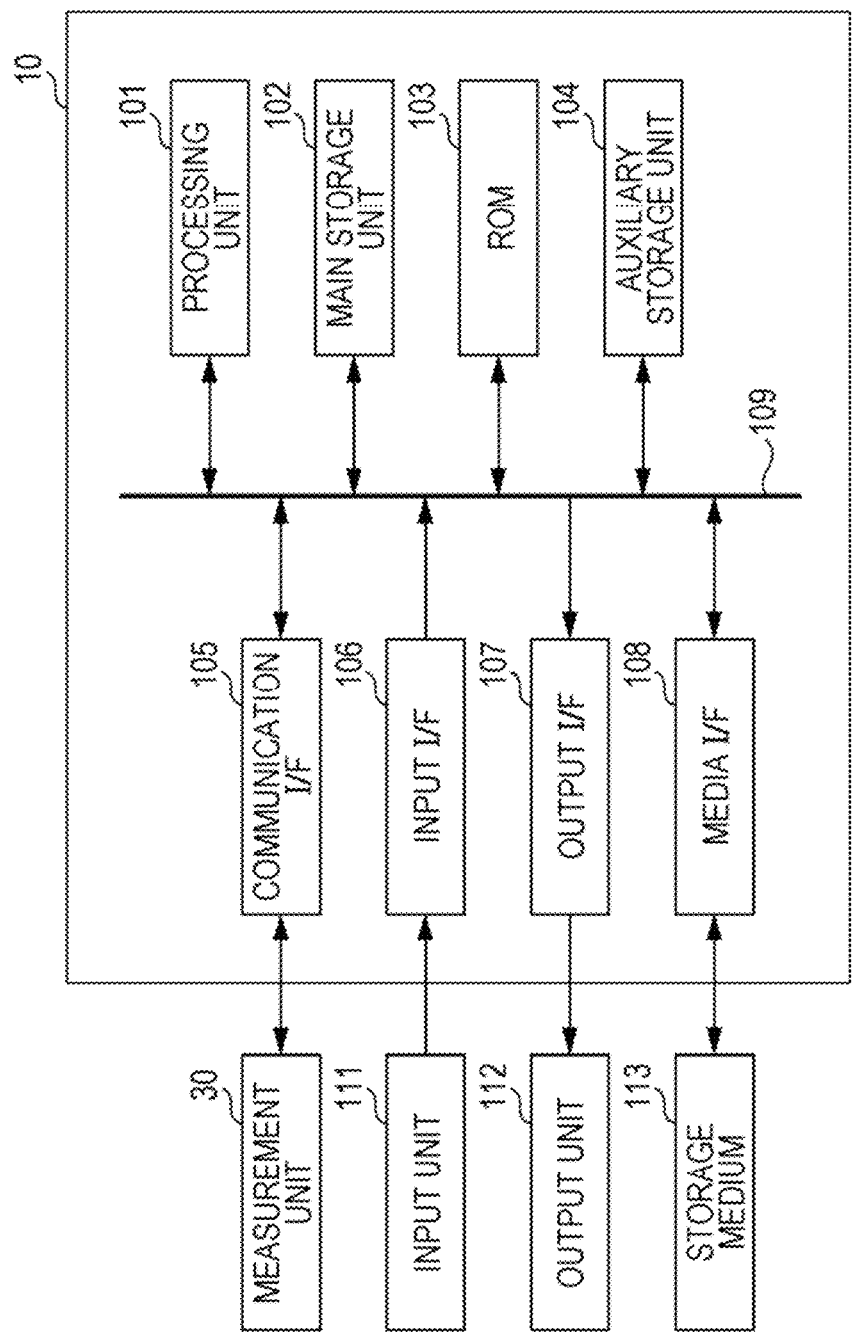
FIG. 2 is a diagram showing an outline of hardware of the apparatus.

FIG. 1 and FIG. 2 show the configuration of the apparatus 10. The apparatus 10 may be connected to an input unit 111, an output unit 112, and a storage medium 113. The apparatus 10 may be connected to a measurement unit 30 that performs ELISA measurement or the like. That is, the apparatus 10 may constitute a system 50 for acquiring a value relating to VEGF-A of a subject, that is connected to the measurement unit 30 directly or via a network or the like.

In the apparatus 10, a processing unit 101, a main storage unit 102, a ROM (read only memory) 103, an auxiliary storage unit 104, a communication interface (I/F) 105, an input interface (I/F) 106, an output interface (I/F) 107 and a media interface (I/F) 108 are data-communicably connected with each other via a bus 109.

The processing unit 101 is configured by a CPU, an MPU, a GPU, or the like. The processing unit 101 executes a computer program stored in the auxiliary storage unit 104 or the ROM 103 and processes data to be acquired so that the apparatus 10 functions.

The ROM 103 is configured by a mask ROM, a PROM, an EPROM, an EEPROM and the like, and a computer program executed by the processing unit 101 and data used for the computer program are recorded in the ROM 103. When starting the apparatus 10, the ROM 103 stores a boot program executed by the processing unit 101 and programs and settings related to the operation of hardware of the apparatus 10.

The main storage unit 102 is configured by a RAM (Random Access Memory) such as SRAM or DRAM. The main storage unit 102 is used for reading the computer program recorded in the ROM 103 and the auxiliary storage unit 104. The main storage unit 102 is used as a work area when the processing unit 101 executes these computer programs. The auxiliary storage unit 102 temporarily stores reference values and the like acquired via the network.

The auxiliary storage unit 104 is configured by a semiconductor memory element such as a hard disk and a flash memory, an optical disk, and the like. In the auxiliary storage unit 104, various computer programs to be executed by the processing unit 101, such as operating systems and application programs, and various setting data used for executing computer programs are stored. Specifically, reference values and the like are stored in a nonvolatile manner.

The communication I/F 105 is configured by a serial interface such as USB, IEEE1394 and RS-232C, a parallel interface such as SCSI, IDE, and IEEE1284, an analog interface including a D/A convener and an A/D converter, a network interface controller (Network interface controller: NIC), and the like. Under the control of the processing unit 101, the communication I/F 105 receives the data from the measurement unit 30 or another external device, and the communication I/F 105 transmits or displays information stored in or generated by the apparatus 10 as necessary to the measurement unit 30 or to the outside. The communication I/F 105 may communicate with the measurement unit 30 or another external device (not shown, for example, another computer, or a cloud system) via a network.

The input I/F 106 is configured by, for example, a serial interface such as USB, IEEE1394, and RS-232C, a parallel interface such as SCSI, IDE, and IEEE1284, an analog interface including a D/A converter, an A/D converter, and the like. The input I/F 106 receives character input, click, voice input and the like from the input unit 111. The received input content is stored in the main storage unit 102 or the auxiliary storage unit 104.

The input unit 111 is configured by a touch panel, a keyboard, a mouse, a pen tablet, a microphone, and the like. The input unit 111 performs character input or voice input to the apparatus 10. The input unit 111 may be connected from the outside of the apparatus 10 or integrated with the apparatus 10.

The output I/F 107 is configured by, for example, the same interface as the input I/F 106. The output I/F 107 outputs the information generated by the processing unit 101 to the output unit 112. The output I/F 107 outputs the information generated by the processing unit 101 and stored in the auxiliary storage unit 104, to the output unit 112.

The output unit 112 is configured by, for example, a display, a printer, and the like. The output unit 112 displays the measurement results transmitted from the measurement unit 30, various operation windows in the apparatus 10, analysis results, and the like.

The media I/F 108 reads, for example, application software or the like stored in the storage medium 113. The read application software or the like is stored in the main storage unit 102 or the auxiliary storage unit 104. The media I/F 108 writes the information generated by the processing unit 101 in the storage medium 113. The media I/F 108 writes the information generated by the processing unit 101 and stored in the auxiliary storage unit 104 to the storage medium 113.

The storage medium 113 is configured by a flexible disk, CD-ROM, DVD-ROM, or the like. The storage medium 113 is connected to the media I/F 108 by a flexible disk drive, a CD-ROM drive, a DVD-ROM drive, or the like. In the storage medium 113, an application program or the like for allowing the computer to execute operation may be stored.

The processing unit 101 may acquire application software and various settings necessary for controlling the apparatus 10 via a network, instead of reading from the ROM 103 or the auxiliary storage unit 104. The application program is stored in the auxiliary storage unit of the server computer on the network, and it is also possible that the apparatus 10 accesses the server computer to download the computer program and store it in the ROM 103 or the auxiliary storage unit 104.

In the ROM 103 or the auxiliary storage unit 104, an operation system for providing a graphical user interface environment such as Windows (registered trademark) manufactured and sold by Microsoft Corporation is installed, it is assumed that the application program according to the second embodiment operates on the operating system. That is, the apparatus 10 may be a personal computer or the like.

[2-2. Operation of Apparatus]

Next, the operation of the apparatus 10 will be described with reference to FIGS. 3 to 7. The operation of the apparatus 10 is controlled by the processing unit 101 of the apparatus 10 in accordance with a computer program which makes a computer execute a step for acquiring a value relating to VEGF-A of a subject to be described later. Acquisition of the value relating to VEGF-A may be an operation that the processing unit 101 takes a total VEGF-A measured value, and/or VEGF-$A_{165}$b/total VEGF-A in the processing unit 101, the main storage unit 102 or the auxiliary storage unit 104 as a value. In the case where the value relating to VEGF-A is a total VEGF-A measured value, acquisition of the value relating to VEGF-A may be an operation that measured raw data such as absorbance acquired by the measurement unit 30, and/or the measured value is taken in the processing unit 101, the main storage unit 102 or the auxiliary storage unit 104. In the case where the value relating to VEGF-A is VEGF-$A_{165}$b/total VEGF-A, acquisition of the value relating to VEGF-A may be an operation that measured raw data such as absorbance on the total VEGF-A and VEGF-$A_{165}$b acquired by the measurement unit 30, and/or the measured value is taken in the processing unit 101, the main storage unit 102 or the auxiliary storage unit 104, and the processing unit 101 calculates VEGF-$A_{165}$b/total VEGF-A. In the case where the value relating to VEGF-A is VEGF-$A_{165}$b/total VEGF-A, acquisition of the value relating to VEGF-A may be an operation that the processing unit 101 calculates VEGF-$A_{165}$b/total VEGF-A, from the total VEGF-A measured value and the VEGF-$A_{165}$b measured value stored in the main storage unit 102 or the auxiliary storage unit 104. In the system 50, acquisition of the measured value may be the start of measurement in the measurement unit 30.

Figure 3:
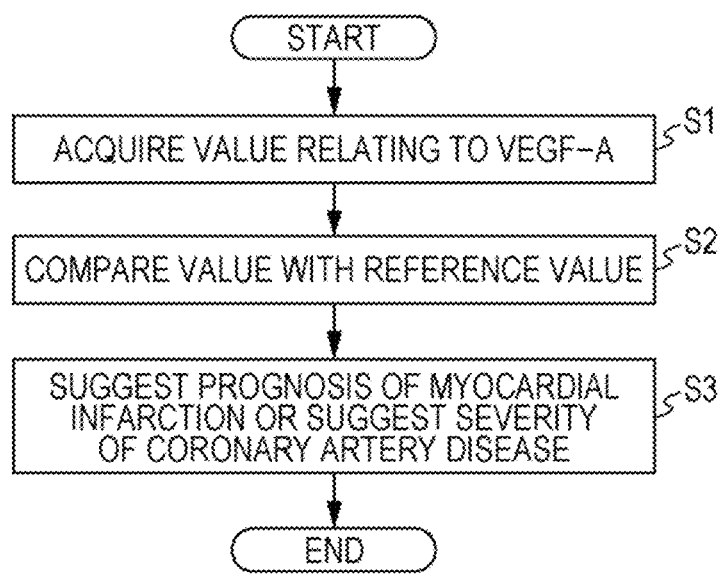
FIG. 3 is a flowchart showing an operation of the apparatus.

First, an outline of the operation of the apparatus 10 for acquiring the value relating to VEGF-A will be described with reference to FIG. 3.

In accordance with a start command for acquiring the value relating to VEGF-A, inputted from the input unit 111 by an examiner or the like, the processing unit 101 acquires the value relating to VEGF-A in the blood sample of the subject acquired by the method described in 1. above (Step S1).

The processing unit 101 compares the value acquired in Step S1 with the corresponding reference value stored in the main storage unit 102 or the auxiliary storage unit 104 (Step S2).

Subsequently, the processing unit 101 suggests prognosis of myocardial infarction of the subject or severity of coronary artery disease of the subject, based on the comparison result of Step S2 (Step S3).

Prior to Step S3, at the same as Step S3, or after Step S3, the processing unit 101 may store the suggestion result on the subject in the auxiliary storage unit 104, the processing unit 101 may output the suggestion result on the subject to the output unit 112, and/or the processing unit 101 may transmit the suggestion result on the subject to the external device (not shown).

Figure 4:
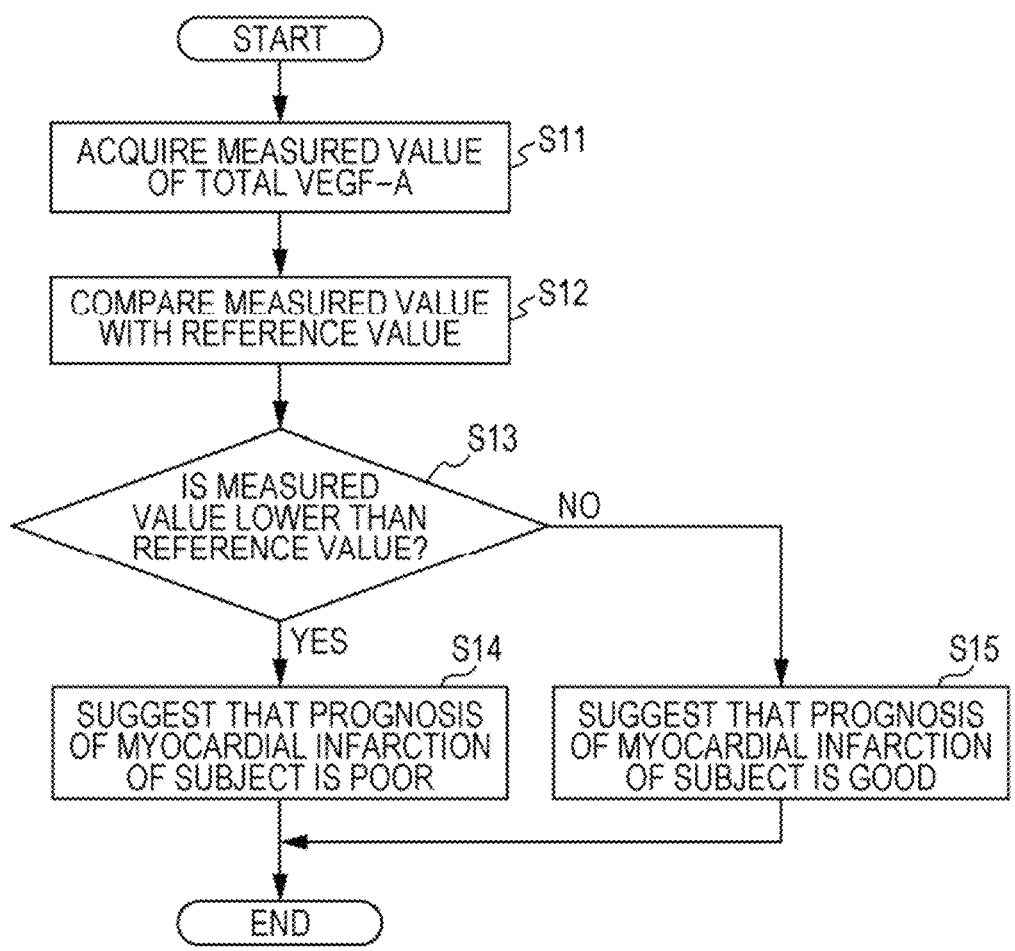
FIG. 4 is a flowchart showing an operation of the apparatus.

Next, the operation of the apparatus 10 for suggesting prognosis of myocardial infarction of a subject using the measured value of total VEGF-A as the value relating to VEGF-A will be described (FIG. 4).

In accordance with a start command for acquiring the value relating to VEGF-A, inputted from the input unit 111 by an examiner or the like, the processing unit 101 acquires the measured value of total VEGF-A in the blood sample of the subject acquired by the method described in 1. above (Step S11).

The processing unit 101 compares the measured value acquired in Step S11 with the corresponding reference value stored in the main storage unit 102 or the auxiliary storage unit 104 (Step S12).

Subsequently, in the comparison of Step S12, the processing unit 101 determines whether or not the measured value of total VEGF-A of the subject is lower than the reference value (Step S13), and when the measured value of total VEGF-A is lower than the reference value, the processing unit 101 proceeds to Step S14 and suggests that the prognosis of myocardial infarction of the subject is poor. When the measured value of total VEGF-A is higher than the reference value, the processing unit 101 proceeds to Step S15 and suggests that the prognosis of myocardial infarction of the subject is good.

Prior to Step S14 or Step S15, at the same time as Step S14 or Step S15, or after Step S14 or Step S15, the processing unit 101 may store the suggestion result on the subject in the auxiliary storage unit 104, the processing unit 101 may output the suggestion result on the subject to the output unit 112, and/or the processing unit 101 may transmit the suggestion result on the subject to the external device (not shown).

Figure 5:
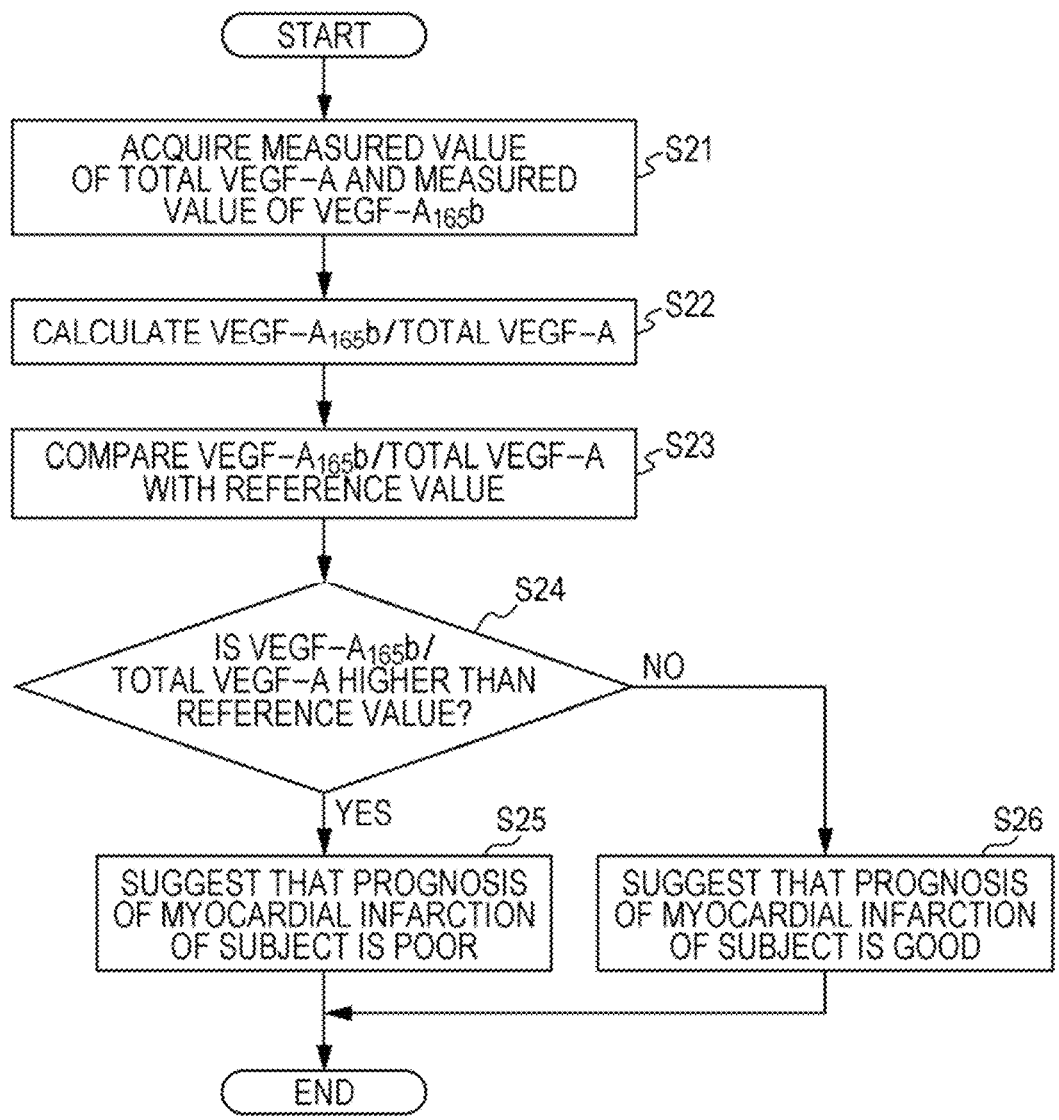
FIG. 5 is a flowchart showing an operation of the apparatus.

Next, the operation of the apparatus 10 for suggesting the prognosis of myocardial infarction of a subject using VEGF-$A_{165}$b/total VEGF-A as the value relating to VEGF-A will be described (FIG. 5).

In accordance with a start command for acquiring the value relating to VEGF-A, inputted from the input unit 111 by an examiner or the like, the processing unit 101 acquires the measured value of total VEGF-A and the measured value of VEGF-$A_{165}$b in the blood sample of the subject acquired by the method described in 1. above (Step S21).

The processing unit 101 obtains VEGF-$A_{165}$b/total VEGF-A by dividing the measured value of VEGF-$A_{165}$b acquired in Step S21 by the measured value of total VEGF-A (Step S22). If necessary, the processing unit 101 may store VEGF-$A_{165}$b/total VEGF-A in the main storage unit 102 and/or the auxiliary storage unit 104 (not shown).

The processing unit 101 compares the VEGF-$A_{165}$b/total VEGF-A acquired in Step S22 with the corresponding reference value stored in the main storage unit 102 or the auxiliary storage unit 104 (Step S23).

Subsequently, in the comparison in Step S23, the processing unit 101 determines whether or not VEGF-$A_{165}$b/total VEGF-A of the subject is higher than the reference value (Step S24), and when VEGF-$A_{165}$b/total VEGF-A is higher than the reference value, the processing unit 101 proceeds to Step S25 and suggests that the prognosis of myocardial infarction of the subject is poor. When VEGF-$A_{165}$b/total VEGF-A is lower than the reference value, the processing unit 101 proceeds to Step S26 and suggests that the prognosis of myocardial infarction of the subject is good.

Prior to Step S25 or Step S26, at the same time as Step S25 or Step S26, or after Step S25 or Step S26, the processing unit 101 may store the suggestion result on the subject in the auxiliary storage unit 104, the processing unit 101 may output the suggestion result on the subject to the output unit 112, and/or the processing unit 101 may transmit the suggestion result on the subject to the external device (not shown).

Figure 6:
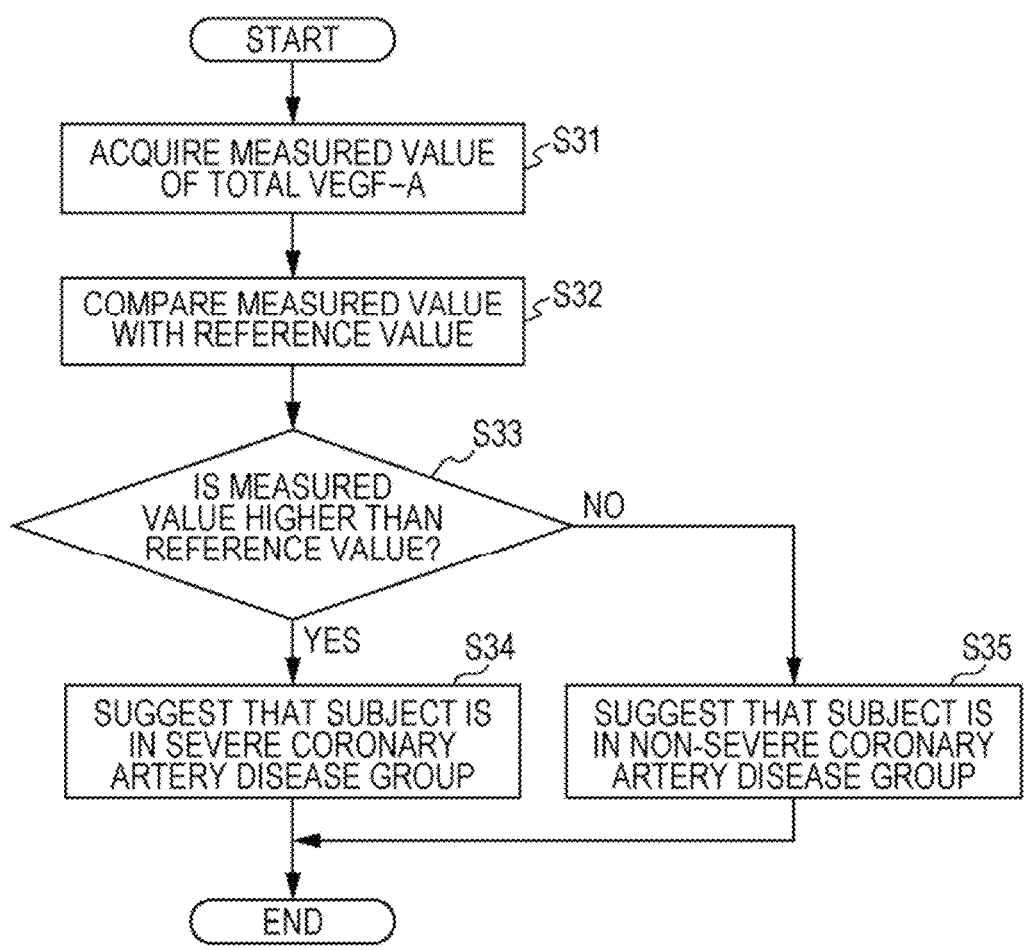
FIG. 6 is a flowchart showing an operation of the apparatus.

Next, the operation of the apparatus 10 for suggesting the severity of coronary artery disease of a subject using the measured value of total VEGF-A as the value relating to VEGF-A will be described (FIG. 6).

In accordance with a start command for acquiring the value relating to VEGF-A, inputted from the input unit 111 by an examiner or the like, the processing unit 101 acquires the measured value of total VEGF-A in the blood sample of the subject acquired by the method described in 1. above (Step S31).

The processing unit 101 compares the measured value acquired in Step S31 with the corresponding reference value stored in the main storage unit 102 or the auxiliary storage unit 104 (Step S32).

Subsequently, in the comparison of Step S32, the processing unit 101 determines whether or not the measured value of total VEGF-A of the subject is higher than the reference value (Step S33), and when the measured value of total VEGF-A is higher than the reference value, the processing unit 101 proceeds to Step S34 and suggests that the subject belongs to a severe group of coronary artery disease. When the measured value of total VEGF-A is lower than the reference value, the processing unit 101 proceeds to Step S35 and suggests that the subject belongs to a non-severe group of coronary artery disease.

Prior to Step S34 or Step S35, at the same time as Step S34 or Step S35 or after Step S34 or Step S35, the processing unit 101 may store the suggestion result on the subject in the auxiliary storage unit 104, the processing unit 101 may output the suggestion result on the subject to the output unit 112, and/or the processing unit 101 may transmit the suggestion result on the subject to the external device (not shown).

Figure 7:
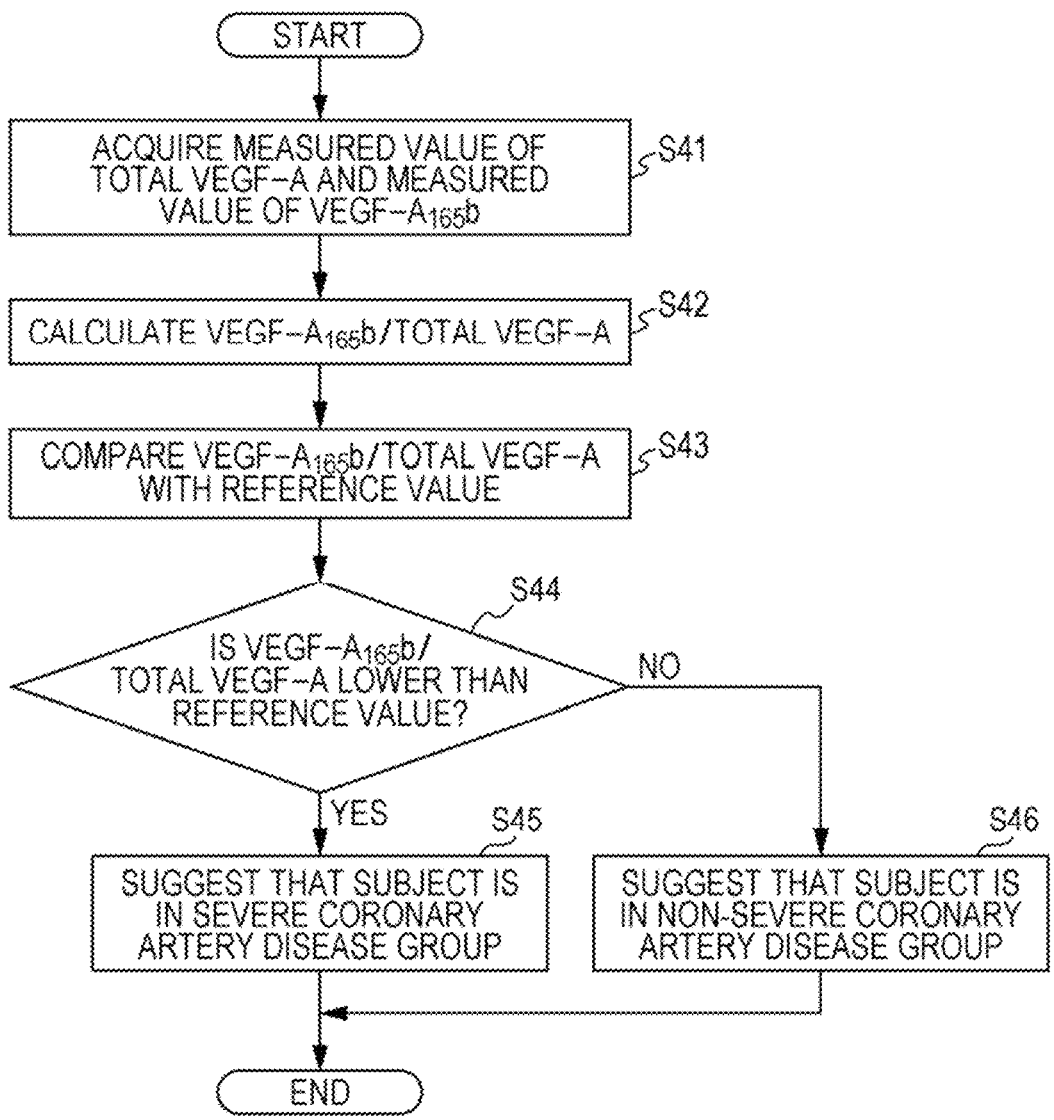
FIG. 7 is a flowchart showing an operation of the apparatus.

Next, the operation of the apparatus 10 for suggesting the severity of coronary artery disease of a subject using VEGF-$A_{165}$b/total VEGF-A as the value relating to VEGF-A will be described (FIG. 7).

In accordance with a start command for acquiring the value relating to VEGF-A, inputted from the input unit 111 by an examiner or the like, the processing unit 101 acquires the measured value of total VEGF-A and the measured value of VEGF-$A_{165}$b in the blood sample of the subject acquired by the method described in 1. above (Step S41).

The processing unit 101 obtains VEGF-$A_{165}$b/total VEGF-A by dividing the measured value of VEGF-$A_{165}$b acquired in Step S41 by the measured value of total VEGF-A (Step S42). If necessary, the processing unit 101 may store VEGF-$A_{165}$b/total VEGF-A in the main storage unit 102 and/or the auxiliary storage unit 104 (not shown).

The processing unit 101 compares the VEGF-$A_{165}$b/total VEGF-A acquired in Step S42 with the corresponding reference value stored in the main storage unit 102 or the auxiliary storage unit 104 (Step S43).

Subsequently, in the comparison in Step S43, the processing unit 101 determines whether or not VEGF-$A_{165}$b/total VEGF-A of the subject is lower than the reference value (Step S44), and when $\text{VEGF-A}_{165}\text{b}/\text{total VEGF-A}$ is lower than the reference value, the processing unit 101 proceeds to Step S45 and suggests that the subject belongs to a severe group of coronary artery disease. When $\text{VEGF-A}_{165}\text{b}/\text{total VEGF-A}$ is higher than the reference value, the processing unit 101 proceeds to Step S46 and suggests that the subject belongs to a non-severe group of coronary artery disease.

Prior to Step S45 or Step S46, at the same time as Step S45 or Step S46 or after Step S45 or Step S46, the processing unit 101 may store the suggestion result on the subject in the auxiliary storage unit 104, the processing unit 101 may output the suggestion result on the subject to the output unit 112, and/or the processing unit 101 may transmit the suggestion result on the subject to the external device (not shown).

[3. Program and Storage Medium Storing Computer Program]

The computer program makes a computer execute a step of acquiring a value relating to VEGF-A. The computer program makes a computer function as an apparatus 10 for acquiring a value relating to VEGF-A of a subject. Specifically, the computer program is a program that makes the computer execute at least one of Steps S1 to S3, Steps S11 to S15, Steps S21 to S26, Steps S31 to S35, and Steps S44 to S46 described in 2-1. above. The program may be a computer program for controlling the computer to realize the methods as defined in claims 1 to 12.

The description of each step described in 2-1. above is incorporated herein by reference. In the description of the apparatus 10, the operation of the apparatus 10, and the computer program, for the terms common to the terms described in 1-1. above, the description of 1-1. above is incorporated herein.

The computer program may be stored in a storage medium. That is, the computer program is stored in a semiconductor memory element such as a hard disk or a flash memory, or a storage medium such as an optical disk. The computer program may be stored in a storage medium connectable via a network such as a cloud server. The computer program may be in a download form or a program product stored in the storage medium.

The storage format of the program in the storage medium is not limited as long as the presented apparatus can read the program. Storage into the storage medium is preferably nonvolatile.

[4. Test Reagent and Kit]

Figure 8:
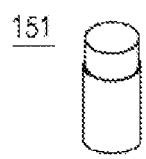
FIG. 8 is a view showing an outline of a test reagent.

A test reagent contains an anti-total VEGF-A antibody, or an anti-$\text{VEGF-A}_{165}\text{b}$ antibody. The antibody may be labeled with, for example, biotin or the like. FIG. 8 is a schematic view of a container 151 storing the test reagent. In the container 151, the antibody is stored as a test reagent in a state of being dissolved in a dry product or a solvent such as a buffer solution (for example, PBS).

Figure 9:
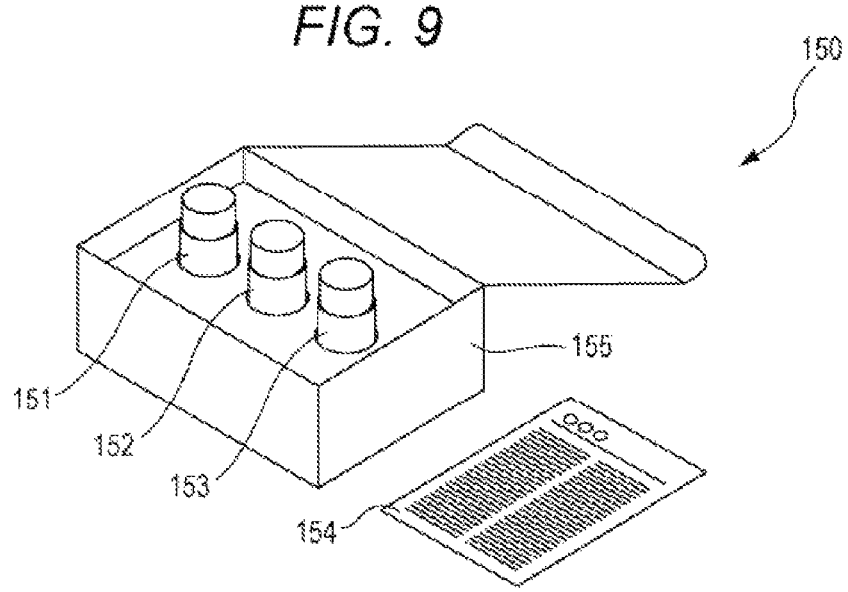
FIG. 9 is a view showing an outline of a kit.

A kit contains at least the test reagent. FIG. 9 shows a schematic view of a kit 150.

The kit 150 includes the container 151 containing a test reagent, and a container 152 storing an anti-total VEGF-A antibody or an anti-$\text{VEGF-A}_{165}\text{b}$ antibody labeled for detection, and a container 153 storing a detection reagent (a luminescent substrate or the like) as necessary. The reagent kit 150 may contain an instruction manual or a sheet 154 describing URL in which the instruction manual can be browsed. The reagent kit 150 may further contain a box 155 containing these containers. Although not shown, the kit may include a solid phase for immobilizing a target protein and a capture antibody.

The test reagent and kit are used for acquiring the measured value relating to VEGF-A described in 1. above, for the purpose of suggesting the prognosis of myocardial infarction of a subject or the severity of coronary artery disease of the subject.

Although the apparatus 10, the operation of the apparatus 10, the computer program, the test reagent and the kit have been described in detail with reference to the accompanying drawings, the present invention is not limited to the specific embodiments described above. The embodiments can be modified based on the description of this specification and technical common knowledge of those skilled in the art.

EXAMPLES

Hereinafter, the present invention will be described in more detail by way of examples, but the present invention is not to be construed as being limited to the examples.

The total VEGF-A concentration and the $\text{VEGF-A}_{165}\text{b}$ concentration in the blood sample was measured in accordance with the ethical principles of the Helsinki Declaration with the approval of Department of Ethics Review Committee, Nagoya University Graduate School of Medicine.

I. Example 1: Acquisition of Measured Value Relating to VEGF-A in Blood Sample after Onset of Myocardial Infarction 1. Measuring Object Person From July 2015 to February 2017, 66 AMI patients who underwent percutaneous coronary intervention (PCI) within 24 hours of onset of symptoms at Nagoya University Hospital were evaluated. Patients with hemodialysis (n=4), patients with active malignancies requiring surgical treatment or chemotherapy in the previous year (n=5), and patients with collagen disease (n=2) were excluded. It is because these diseases may affect total VEGF-A concentration and $\text{VEGF-A}_{165}\text{b}$ concentration. Blood samples could be eventually collected on Day 3 and Day 30 of hospitalization after onset of AMI, and the total VEGF-A concentration and the $\text{VEGF-A}_{165}\text{b}$ concentration could be measured in 23 patients. The breakdown of 23 patients and their clinical data are shown in Table 1-1 and Table 1-2.

TABLE 1-1

| | | MACCE | | |
| --- | --- | --- | --- | --- |
| Variables | All (n = 23) | No (n = 14) | Yes (n = 9) | p value |
| Age (years) | 67.0 ± 10.8 | 64.3 ± 11.3 | 71.2 ± 9.0 | 0.14 |
| Male, n (%) | 17 (73.9) | 11 (78.5) | 6 (66.7) | 0.44 |
| Body mass index (kg/m$^2$) | 22.9 ± 2.9 | 23.2 ± 3.0 | 22.4 ± 3.0 | 0.54 |
| Current smoking, n (%) | 7 (30.4) | 4 (28.6) | 3 (33.3) | 0.58 |
| Hypertension, n (%) | 10 (43.5) | 6 (42.9) | 4 (44.4) | 0.64 |
| Diabetes mellitus, n (%) | 7 (30.4) | 5 (35.7) | 2 (22.2) | 0.42 |

TABLE 1-1-continued

| Variables | All (n = 23) | MACCE No (n = 14) | MACCE Yes (n = 9) | p value |
|---|---|---|---|---|
| Dyslipidemia, n (%) | 16 (69.6) | 10 (71.4) | 6 (66.7) | 0.58 |
| eGFR (mL/min/1.73 m$^2$) | 60.9 (57.0-71.8) | 62.1 (58.8-74.1) | 59.5 (54.2-68.4) | 0.40 |
| LDL cholesterol (mg/dL) | 133.3 ± 28.7 | 136.5 ± 29.6 | 128.3 ± 28.1 | 0.52 |
| HDL cholesterol (mg/dL) | 50.1 ± 11.4 | 49.0 ± 10.2 | 51.9 ± 13.4 | 0.56 |
| Triglycerides (mg/dL) | 182.4 ± 102.7 | 187.3 ± 93.2 | 174.8 ± 121.5 | 0.78 |
| Hemoglobin A1c (%) | 5.8 (5.7-6.8) | 5.9 (5.8-6.9) | 5.8 (5.6-6.6) | 0.64 |
| C-reactive protein (mg/L) | 1.0 (0.7-2.5) | 1.0 (0.7-4.8) | 0.8 (0.7-3.0) | 0.56 |
| Peak creatine kinase (IU/L) | 2443 (1639-4694) | 2874 (1874-5148) | 2443 (1479-4491) | 0.56 |
| Creatine kinase (AUC) (IU/L × h) | 43142 (29788-88934) | 51164 (31922-92034) | 40748 (18932-78411) | 0.69 |
| Peripheral artery disease, n (%) | 2 (8.7) | 1 (7.1) | 1 (11.1) | 0.66 |
| Duration of hospital stay (days) | 12 (8-16) | 12 (9-17) | 11 (8-20) | 0.98 |
| Time to reperfusion (min) | 90.9 ± 31.9 | 85.6 ± 24.9 | 98.4 ± 40.4 | 0.37 |
| Culprit lesion (LAD (%), LCX (%), RCA (%)) | 56.5, 13.0, 30.4 | 21.4, 57.1, 21.4 | 44.4, 55.6, 0 | 0.10 |
| Multivessel disease, n (%) | 7 (30.4) | 5 (35.7) | 2 (22.2) | 0.42 |
| Killip class (I (%), II (%), III (%), IV (%)) | 69.6, 4.3, 8.7, 17.4 | 78.6, 0, 0, 21.4 | 55.6, 11.1, 22.2, 11.1 | 0.40 |

TABLE 1-2

| Variables | All (n = 23) | MACCE No (n = 14) | MACCE Yes (n = 9) | p value |
|---|---|---|---|---|
| TIMI flow grade before PCI (0(%), 1(%), 2(%), 3(%)) | 73.9, 4.3, 13, 8.7 | 57.1, 7.1, 21.4, 14.2 | 100, 0, 0, 0 | 0.030 |
| TIMI flow grade after PCI (0(%), 1(%), 2(%), 3(%)) | 0, 4.3, 4.3, 91.3 | 0, 0, 7.1, 92.9 | 0, 11.1, 0, 88.9 | 0.39 |
| LVEF after PCI (%) | 53.3 ± 10.9 | 55.6 ± 8.3 | 49.7 ± 13.8 | 0.21 |
| Medication on admission | | | | |
| Antiplatelet agents, n (%) | 2 (8.7) | 1 (7.1) | 1 (11.1) | 0.64 |
| ACE-I or ARB, n (%) | 8 (34.8) | 6 (42.9) | 2 (22.2) | 0.29 |
| Beta-blocker, n (%) | 2 (8.7) | 1 (7.1) | 1 (11.1) | 0.64 |
| Calcium channel blocker, n (%) | 5 (21.7) | 3 (21.4) | 2 (22.2) | 0.67 |
| Statin, n (%) | 5 (21.7) | 4 (28.6) | 1 (11.1) | 0.33 |
| Medication at discharge | | | | |
| Antiplatelet agents, n (%) | 23 (100) | 14 (100) | 9 (100) | |
| ACE-I or ARB, n (%) | 21 (91.3) | 13 (92.9) | 8 (88.9) | 0.64 |
| Beta-blocker, n (%) | 14 (60.9) | 10 (71.4) | 4 (44.4) | 0.20 |
| Calcium channel blocker, n (%) | 3 (13.0) | 2 (14.3) | 1 (11.1) | 0.67 |
| Statin, n (%) | 22 (95.7) | 13 (92.9) | 9 (100) | 0.61 |

Data in Tables 1-1 and 1-2 indicate mean±SD or median (interquartile range), or number (percentage). In Tables 1-1 and 1-2, MACCE means major adverse cardiac and cerebrovascular events. Abbreviations in Table 1-1 or Table 1-2 mean as follows: eGFR: estimated glomerular filtration rate; LDL: low density lipoprotein, HDL: high density lipoprotein; AUC: area under concentration versus time curve; LAD: left anterior descending artery; LCX: left circumflex coronary artery; RCA: right coronary artery; Culprit lesion: responsible lesion; TIMI: thrombolysis in myocardial infarction; LVEF: left ventricular ejection fraction; PCI: percutaneous coronary intervention; ACE-I: angiotensin-converting enzyme inhibitor; and ARB: angiotensin receptor blocker.

2. Clinical Definition and Endpoint

AMI was diagnosed according to the third universal definition of myocardial infarction (Circulation 2012; 126: 2020-2035). The primary endpoint was a complex of cardiovascular death, recurrent nonfatal myocardial infarction (MI), reapplication of coronary artery revascularization surgery and cerebral infarction after AMI. Cardiovascular death was defined as death from a cardiovascular cause within 24 hours after onset. Recurrent nonfatal MI was diagnosed using the criteria of the third universal definition of myocardial infarction. Coronary artery revascularization surgery was defined as PCI or coronary artery bypass grafting (CABG) associated with progressive stenosis in in-stent restenosis or non-responsible lesion. By using quantitative coronary angiography (QCA), the non-responsible lesion was defined as a lesion whose diameter stenosis (DS) was 50% or less in QCA at primary PCI (PCI at the first onset of myocardial infarction). Progression means that the stenotic lesion has newly progressed to a non-responsible lesion at a later date after the first myocardial infarction and was defined as a lesion with a DS exceeding 50%. QCA was performed using a cardiovascular measurement system (QCA-CMS version 7.2, MEDIS, Leiden, the Netherlands). Cerebral infarction was defined as a newly developed neurological deficit on magnetic resonance imaging. Information on MACCE was collected from hospital medical records or by phone interviews with patients or their families. The breakdown of MACCE is shown in Table 2. Hypertension was defined as the case of having a baseline blood pressure ≥140/90 mmHg, and/or using an antihypertensive drug was used. Dyslipidemia was defined as the case of having triglycerides ≥150 mg/dL, low density lipoprotein cholesterol ≥140 mg/dL, high density lipoprotein cholesterol ≤40 mg/dL, and/or using an antilipemic drug. Diabetes mellitus was defined as the case of having a fasting plasma glucose concentration >126 mg/dL, a glycosylated hemoglobin concentration ≥6.5% (National Glycohemoglobin Standardization Program), and/or using an antidiabetic drug. Current smoking was defined as those who declared active smoking. Peripheral arterial disease (PAD) was defined as the case of having an ankle brachial index <0.9, claudication of PAD, and/or previously undergoing revascularization surgery.

TABLE 2

| Major adverse cardiac and cerebrovascular events (MACCE) | |
|---|---|
| Cardiovascular death, n (%) | 0 (0) |
| Recurrent nonfatal myocardial infarction, n (%) | 1 (4.3) |
| Reapplication of coronary artery revascularization surgery, n (%) | 7 (30.4) |
| Cerebral infarction, n (%) | 1 (4.3) |

3. Acquisition of Measured Value Relating to VEGF-A

Blood samples were collected on Day 3 and Day 30 after onset of AMI, and serum was separated and stored at −80° C. until measurement. The serum VEGF-A concentration was measured using an enzyme-linked immunosorbent assay (ELISA) kit (human VEGF Quantikine ELISA kit. DVE00, R&D) according to the protocol attached to the kit. The detection limit was 9 pg/mL. The coefficient of variation in the assay and between the assays were 4.5% and 7.0%, respectively. The serum VEGF-$A_{165}$b concentration was measured using an ELISA kit (human vascular endothelial growth factor-$_{165}$b ELISA kit, MBS720132, MyBiosource) according to the protocol attached to the kit. The detection limit was 1 pg/mL. The coefficient of variation in the assay and between the assays were <10% and <10%, respectively.

4. Statistical Analysis

Continuous value data was shown as mean±standard deviation of normal distribution variables or median (quartile range; IQR) of non-normal distribution data. Categorical variables are expressed as a numerical value (percentage). The difference between the continuous values of the normal distribution was evaluated using the Student's t-test, and the non-normal distribution value was evaluated using Mann-Whitney's U test. Differences in categorical variables were evaluated using the Kruskal-Wallis test or chi-square test. Kaplan-Meier analysis was performed to evaluate the cumulative incidence of MACCE, and the comparison was evaluated using a log-rank test. The MACCE cut-off value was calculated using a receiver operating characteristic curve (ROC) analysis. When multiple events occurred for individual patients, Kaplan-Meier analysis was performed only on the day of the first event. A p value <0.05 was considered to be statistically significant. All statistical analyzes were performed using SPSS version 23 (SPSS Inc., Chicago, Ill., USA).

5. Results

The results of comparing the total VEGF-A concentration, the VEGF-$A_{165}$b concentration and the ratio of VEGF-$A_{165}$b to total VEGF-A (VEGF-$A_{165}$b/total VEGF-A) in the blood sample in the presence or absence of MACCE are shown in FIG. 10. FIG. 10A shows the total VEGF-A concentration. FIG. 10B shows the VEGF-$A_{165}$b concentration, and FIG. 10C shows VEGF-$A_{165}$b/total VEGF-A. The upper row shows data on Day 3 after the onset of AMI, and the lower row shows data on Day 30 after the onset of AMI.

The total VEGF-A concentration was lower in patients whom MACCE was observed than patients whom MACCE was not observed on Day 3 and Day 30 after the onset of AMI. The difference was remarkable especially on Day 30 (median: 153.6, IQR: [130.6 to 371.4] vs. 301.9 [242.5 to 384.1] pg/mL, p=0.028).

On the other hand, no difference was observed in the presence or absence of MACCE on the VEGF-$A_{165}$b concentrations on Day 3 and Day 30 after the onset of AMI.

VEGF-$A_{165}$b/total VEGF-A was higher in patients whom MACCE was observed than patients whom MACCE was not observed on Day 3 and Day 30 after the onset of AMI (0.70 [0.34 to 0.93] vs. 0.25 [0.21 to 0.62], p=0.039; 0.65 [0.42 to 0.95] vs. 0.36 [0.23 to 0.52], p=0.023).

Figure 11A:
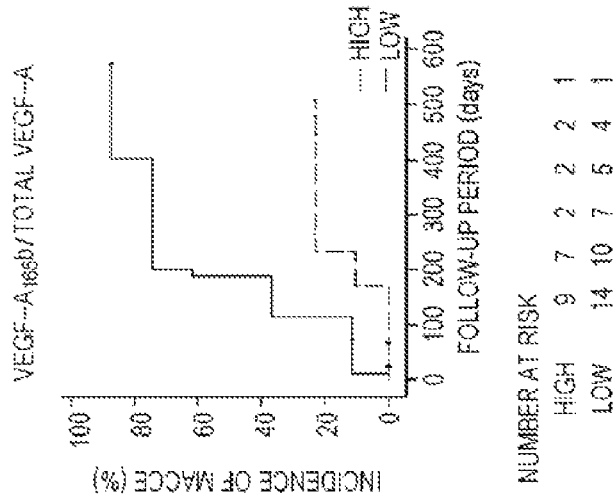
FIG. 11A shows the cumulative incidence of MACCE in the groups in which the measured value of total VEGF-A on Day 30 after the onset of myocardial infarction was lower than (Low: solid line) and higher than (High: dashed line) the reference value.
Figure 11B:
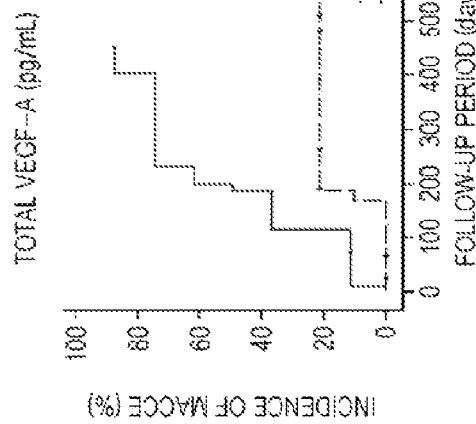
FIG. 11B shows the cumulative incidence of MACCE in the groups in which VEGF-$A_{165}$b/total VEGF-A on Day 30 after the onset of myocardial infarction was lower than (Low: dashed line) and higher than (High: solid line) the reference value.

In order to predict the occurrence of MACCE, the cut-off value was tentatively obtained, based on the total VEGF-A concentration and the value of VEGF-$A_{165}$b/total VEGF-A on Day 30 after the onset of AMI. The cut-off value was determined to 233.1 pg/mL for total VEGF-A (area under the ROC curve [AURC]=0.78, p=0.033), and 0.57 for VEGF-$A_{165}$b/total VEGF-A (AURC=0.79, p=0.015), based on the ROC curve. Graphs of the cumulative incidence of MACCE were created with a group having higher values than the cut-off value as High group and a group having higher values than the cut-off value as Low group (FIGS. 11A and 11B). Significant difference between Low group and High group was obtained by Kaplan-Meier analysis.

The incidence of MACCE in the total VEGF-A Low group was 92%, whereas the incidence of MACCE in the total VEGF-A High group was 22%. Thus, p=0.011 in the log-rank test, and a significant difference was observed. The incidence of MACCE in the VEGF-$A_{165}$b/total VEGF-A High group was 87%, whereas the incidence of MACCE in the VEGF-$A_{165}$b/total VEGF-A Low group was 25%. Thus, p=0.0058 in the log-rank test, and a significant difference was observed.

From this, the total VEGF-A concentration and VEGF-$A_{165}$b/total VEGF-A were considered to be useful markers for prediction of prognosis.

II. Example 2: Acquisition of Measured Values Relating to VEGF-A in Blood Samples of Coronary Artery Disease Patients 1. Measuring Object Person From February 2015 to June 2016 at Nagoya University Hospital, 268 patients who underwent percutaneous coronary intervention (PCI) for stable angina pectoris (AP) or acute coronary syndrome (ACS) were evaluated. These patients included 73 people who received PCI for stable angina pectoris. Exclusion criteria were as follows: (i) patients undergoing hemodialysis (HD) treatment; (ii) patients with active malignancies or patients who underwent malignant tumor surgery or chemotherapy within less than 1 year, (iii) people who underwent PCI or coronary artery bypass grafting for ischemic cardiovascular disease; (iv) people with collagen disease. An observer and a cardiac surgeon confirmed that the examination was appropriate for all patients and was most consistent with the patient's request. As the control group, 32 patients who had no malignant tumor and underwent coronary angiography due to clinical symptoms or electrocardiographic abnormalities but had a SS of 0 were selected. The control group is a group of patients with normal left ventricular function who have not undergone cardiac surgery or dialysis. The control group does not include patients with malignancies. Patients received written consent from all patients prior to evaluation.

The breakdown of patients and their clinical data are shown in Table 3-1 and Table 3-2.

were not informed of identity and clinical information of the patients. Together with the SYNTAX test, subjects who received. PCI were divided into two groups: Low SS group (SS≤22) and High SS group (SS>22). The High SS group includes those with moderate severity of coronary artery disease with 22<SS≤33 and those advanced severity of coronary artery disease with SS>33.

5. Explanation of Terms Used in Example 2

Hypertension was defined as having a systolic blood pressure of 140 mmHg or more, or a diastolic blood pressure

TABLE 3-1

| | | | | PCI subjects (n = 73) | | |
| --- | --- | --- | --- | --- | --- | --- |
| Variable | Control | PCI | P Value | Low SS | High SS | P Value |
| Number of subjects | 32 | 73 | — | 63 | 10 | — |
| Men (%) | 18 (56.3) | 57 (78.1) | 0.03 | 48 (76.2) | 9 (90.0) | 0.44 |
| Age (years) | 70.4 ± 9.8 | 69.9 ± 9.3 | 0.77 | 69.0 ± 9.2 | 75.4 ± 8.2 | 0.04 |
| BMI (kg/m$^2$) | 23.7 ± 4.1 | 24.5 ± 3.4 | 0.34 | 24.6 ± 3.5 | 23.7 ± 3.5 | 0.48 |
| HT (%) | 29 (90.6) | 48 (65.8) | <0.01 | 43 (68.3) | 5 (50.0) | 0.30 |
| DM (%) | 12 (37.5) | 32 (43.8) | 0.67 | 28 (44.4) | 4 (40.0) | 0.79 |
| Current/Ex smoker (%) | 13 (40.6) | 43 (58.9) | 0.09 | 37 (58.7) | 6 (60.0) | 0.94 |
| PAD (%) | 2 (6.3) | 7 (9.6) | 0.72 | 7 (11.1) | 0 (0) | 0.58 |
| eGFR (ml/min/1.73 m$^2$) | 65.8 ± 22.4 | 67.1 ± 21.1 | 0.77 | 67.5 ± 21.0 | 64.4 ± 22.6 | 0.67 |
| LDL (mg/dl) | 104.2 ± 29.0 | 100.8 ± 34.0 | 0.64 | 101.5 ± 36.3 | 96.3 ± 13.0 | 0.43 |
| HDL (mg/dl) | 48.6 ± 10.8 | 46.8 ± 10.4 | 0.43 | 47.3 ± 9.9 | 43.2 ± 13.4 | 0.28 |
| TG (mg/dl) | 108.0 (81.3-153.5) | 117.5 (79.8-170.3) | 0.68 | 119.5 (83.0-169.5) | 103.5 (69.0-185.8) | 0.49 |

TABLE 3-2

| | | | | PCI subjects (n = 73) | | |
| --- | --- | --- | --- | --- | --- | --- |
| Variable | Control | PCI | P Value | Low SS | High SS | P Value |
| Number of subjects | 32 | 73 | — | 63 | 10 | — |
| HbA1c (%) | 6.4 ± 1.1 | 6.3 ± 0.8 | 0.59 | 6.3 ± 0.8 | 6.1 ± 0.7 | 0.46 |
| Plt (×10$^3$/μl) | 211 ± 55.9 | 225 ± 92.6 | 0.43 | 229 ± 9.8 | 200 ± 4.8 | 0.37 |
| CRP (mg/dl) | 0.10 (0.04-0.19) | 0.14 (0.09-0.35) | <0.05 | 0.14 (0.10-0.30) | 0.24 (0.08-1.26) | 0.70 |
| Neutrophils (cells/μl) | 3894 ± 1332.9 | 3858 ± 1793.3 | 0.92 | 3854 ± 1828.7 | 3880 ± 1639.7 | 0.97 |
| Lymphocytes (cells/μl) | 1534 ± 472.2 | 1751 ± 749.8 | 0.14 | 1748 ± 707.0 | 1770 ± 1026.4 | 0.93 |
| LVEF (%) | 67.0 ± 7.3 | 62.7 ± 11.0 | 0.06 | 64.2 ± 10.2 | 56.6 ± 13.4 | <0.05 |
| LV mass Index (g/m$^2$) | 123.7 ± 33.5 | 116.1 ± 35.4 | 0.33 | 111.3 ± 33.2 | 143.7 ± 36.7 | <0.01 |

In Table 3-1 and Table 3-2, the values indicate mean±SD, median (interquartile range) or number (%). Abbreviations in Table 3-1 or Table 3-2 are as follows: PCI: percutaneous coronary intervention, BMI: body mass index, HT: hypertension, DM: diabetes mellitus, PAD: peripheral artery disease, eGFR: estimated glomerular filtration rate, LDL: low density lipoprotein, HDL: high density lipoprotein, TG: triglyceride, HbA1c: hemoglobin A1c, Plt: platelet, CRP: C-reactive protein, and LVEF: left ventricular ejection fraction.

2. Collection of Blood Samples

Blood donors were collected from all patients after an overnight fast of 12 hours and on the day of PCI prior to heparin injection.

3. Acquisition of Measured Value Relating to VEGF-A

Acquisition was carried out in accordance with Example 1.

4. Angiographic Analysis

The complexity of coronary artery lesions was quantified using the SYNTAX score (EuroInvterv. 2005; 1: 219-227). Based on the baseline diagnostic angiogram, coronary artery lesions that caused stenosis of 50% or more diameter in 1.5 mm or more blood vessels were scored individually, and then the total SYNTAX score (SS) calculated using the SYNTAX score algorithm was obtained. Coronary angiograms were analyzed by two experienced surgeons who of 90 mmHg or more, and/or using an antihypertensive drug. Blood pressure was measured after at least 10 minutes of rest in a sitting position using an appropriate arm cuff and mercury sphygmomanometer. Diabetes mellitus was defined as currently being diagnosed as Diabetes mellitus, having a fasting plasma glucose concentration ≥126 mg/dL or a glycosylated hemoglobin (HbA1c) concentration ≥6.5% (National Glycohemoglobin Standardization Program), and/or using any antidiabetic agent. eGFR was calculated according to the following formula (in females): eGFR (mL/min/1.73 m$^2$)=194×serum creatinine$^{-1.094}$×age$^{-0.287}$× 0.739. Peripheral arterial disease (PAD) was defined as having an ankle brachial index (ABI)<0.9, claudication, and/or previously undergoing revascularization surgery. All echocardiographic parameters were measured according to the recommendations of the American Society of Echocardiography. Echocardiograms were obtained with views of the sternum (long and short axis) and apex. In echocardiography, the following parameters were evaluated: left ventricular end diastolic diameter (LVEDD; mm); left ventricular end systolic diameter (LVESD; mm); end-diastolic interventricular septum diameter (IVSd; mm); end-diastolic left ventricular posterior wall diameter (PWd; mm); and LV mass (g). LV mass was indexed based on body surface area (LV mass index; g/m$^2$). The left ventricular ejection fraction (LVEF; %) was calculated based on the method of Biplane Simpson and views of apical four chambers and two chambers.

6. Statistical Analysis

Statistical analysis was carried out based on the method described in Example 1.

7. Results

Figure 12A:
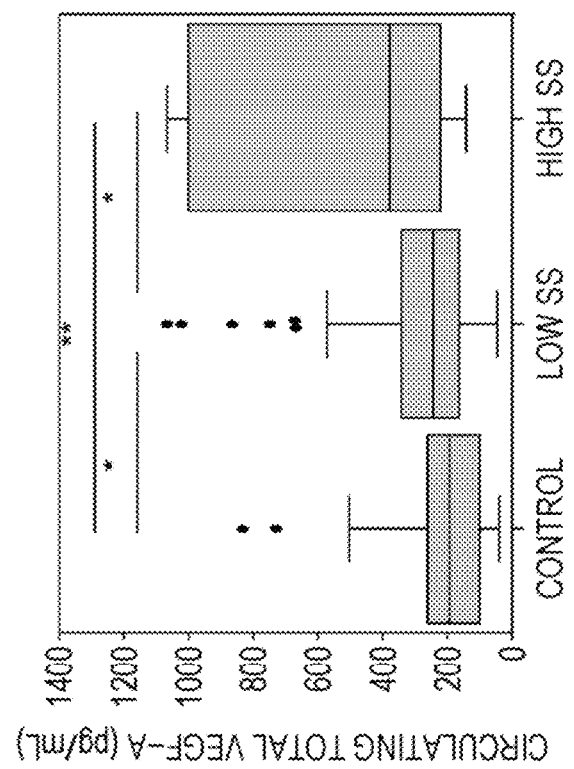
FIG. 12A shows box plots of measured values of total VEGF-A in a control group, a group with a SYNTAX score of 22 or less (Low SS), and a group with a SYNTAX score more than 22 (High SS).
Figure 12B:
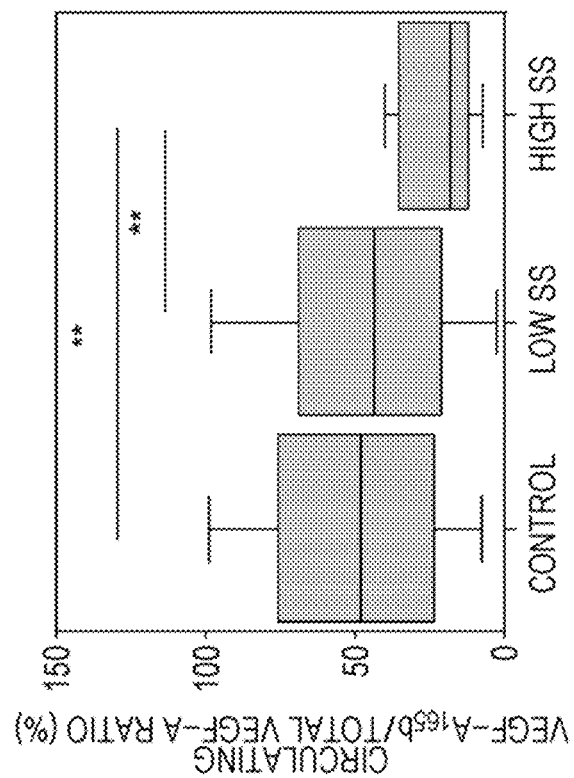
FIG. 12B shows box plots of VEGF-$A_{165}$b/total VEGF-A in a control group, a group with a SYNTAX score of 22 or less (Low SS), and a group with a SYNTAX score more than 22 (High SS).

FIG. 12 shows the total VEGF-A concentration (FIG. 12A) in the blood sample and the ratio of VEGF-$A_{165}$b to total VEGF-A (VEGF-$A_{165}$b/total VEGF-A) (FIG. 12B). As for the total VEGF-A concentration, the average value of the measured values tended to be slightly higher in the Low SS group than in the control group, and the average value of the measured values was much higher in the High SS group than in the control group and the Low SS group (control group 194.4 pg/ml; Low SS group 243.4 pg/ml; High SS group 377.9 pg/ml; control group vs. Low SS group p=0.044; control group vs. High SS group p=0.005; Low SS group vs. High SS group p=0.018).

As for VEGF-$A_{165}$b/total VEGF-A, the average value tended to be slightly lower in the Low SS group than in the control group, and the average value was lower in the High SS group than in the control group and the Low SS group (control group 48.2%; Low SS group 43.5%; High SS group 18.2%; High SS group vs. Low SS group p=0.004; High SS group vs. control group p=0.006).

From the above results, it was revealed that the total VEGF-A concentration and VEGF-$A_{165}$b/total VEGF-A are indicators of the severity of coronary artery lesions. It was considered that the total VEGF-A concentration and VEGF-$A_{165}$b/total VEGF-A can be used as a marker reflecting the SYNTAX score.

What is claimed is:

1. A method for detecting VEGF-A and VEGF-$A_{165}$b in a subject with coronary artery disease or following myocardial infarction, said method comprising:

measuring, by immunoassay using an anti-total VEGF-A antibody, the amount of total VEGF-A in a blood sample obtained from the subject, wherein the amount of total VEGF-A in said sample is measured by detecting, via a detection apparatus, a detectable signal produced by the immunoassay;

measuring, by immunoassay using an antibody that specifically binds to anti-VEGF-$A_{165}$b, the amount of VEGF-$A_{165}$b in said sample, wherein the amount of VEGF-$A_{165}$b in said sample is measured by detecting, via a detection apparatus, a detectable signal produced by the immunoassay, acquiring, by a hardware processor, measurement values for the measured amounts of total VEGF-A and VEGF-$A_{165}$b in said sample;

determining from the acquired measurement values, via the hardware processor, the proportion of total VEGF-A that is VEGF-$A_{165}$b in said sample; and comparing, via the hardware processor, the determined proportion of total VEGF-A that is VEGF-$A_{165}$b in said sample to a corresponding reference proportion, wherein when said subject is a subject following myocardial infarction, said method further comprises determining, via the hardware processor, that the prognosis of the myocardial infarction of the subject is poor when the proportion of total VEGF-A that is VEGF-$A_{165}$b in said sample is higher than the corresponding reference proportion and displaying a result from which a diagnosis may be made based on determining that the prognosis of the myocardial infarction of the subject is poor.

2. The method according to claim 1, wherein said corresponding reference proportion is obtained from a group of subjects having a good prognosis following myocardial infarction.

3. The method according to claim 1, wherein when said subject is a subject following myocardial infarction, said method further comprises determining that the prognosis of the myocardial infarction of the subject is good when the proportion of total VEGF-A that is VEGF-$A_{165}$b in said sample is lower than a corresponding reference proportion.

4. The method according to claim 1, wherein the poor prognosis comprises the high risk of occurrence of major adverse cardiac and cerebrovascular events.

5. The method according to claim 4, wherein the major adverse cardiac and cerebrovascular events comprise one or more events selected from the group consisting of cardiovascular death, recurrence of nonfatal myocardial infarction, reapplication of coronary artery revascularization surgery, and cerebral infarction.

6. The method according to claim 1, wherein when said subject is a subject with coronary artery disease, said method further comprises determining that the subject has severe coronary artery disease when the proportion of total VEGF-A that is VEGF-$A_{165}$b in said sample is lower than a corresponding reference proportion.

7. The method according to claim 6, wherein said severe coronary artery disease has a SYNTAX score of more than 22.

8. The method according to claim 1, wherein when said subject is a subject with coronary artery disease, said method further comprises determining that the subject has non-severe coronary artery disease when the proportion of total VEGF-A that is VEGF-$A_{165}$b in said sample is higher than a corresponding reference proportion.

9. The method according to claim 8, wherein said corresponding reference proportion is obtained from a group of subjects having severe coronary artery disease.

10. The method according to claim 8, wherein said non-severe coronary artery disease has a SYNTAX score of 22 or less.

* * * * *